4,461,691 7/1984 Frank ............................ 204/242

United States Patent [19]
Wrighton et al.

[11] Patent Number: 5,034,192
[45] Date of Patent: Jul. 23, 1991

[54] MOLECULE-BASED MICROELECTRONIC DEVICES

[75] Inventors: Mark S. Wrighton, Winchester; Henry S. White, Jr., Somerville; Gregg P. Kittlesen, Cambridge, all of Mass.

[73] Assignee: Massachusetts Institute of Technology, Cambridge, Mass.

[21] Appl. No.: 370,279

[22] Filed: Jun. 21, 1989

Related U.S. Application Data

[60] Continuation of Ser. No. 49,341, May 13, 1987, Pat. No. 4,895,705, which is a division of Ser. No. 674,410, Nov. 23, 1984, Pat. No. 4,721,601.

[51] Int. Cl.[5] .......................................... G01N 27/00
[52] U.S. Cl. ................................. 422/82.02; 422/90; 422/97; 422/98; 436/151; 436/806; 324/71.5; 324/438; 204/433; 204/435; 204/416; 204/418
[58] Field of Search ................. 422/68.1, 90, 97, 98, 422/82.01, 82.02; 436/151, 806; 324/71.5, 438; 204/433, 435, 418, 416

[56] References Cited

U.S. PATENT DOCUMENTS

| | | | |
|---|---|---|---|
| 3,905,889 | 9/1975 | Macur et al. | 204/418 |
| 3,923,627 | 12/1975 | Niedrach et al. | 204/418 |
| 4,442,422 | 4/1984 | Murata et al. | 422/98 |
| 4,444,892 | 4/1984 | Malmros | 436/151 |

Primary Examiner—Robert J. Warden
Assistant Examiner—Lynn M. Kummert
Attorney, Agent, or Firm—Kilpatrick & Cody

[57] ABSTRACT

Several types of new microelectronic devices including diodes, transistors, sensors, surface energy storage elements, and light-emitting devices are disclosed. The properties of these devices can be controlled by molecular-level changes in electroactive polymer components. These polymer components are formed from electrochemically polymerizable material whose physical properties change in response to chemical changes, and can be used to bring about an electrical connection between two or more closely spaced microelectrodes. Examples of such materials include polypyrrole, polyaniline, and polythiophene, which respond to changes in redox potential. Each electrode can be individually addressed and characterized electrochemically by controlling the amount and chemical composition of the functionalizing polymer. Sensitivity of the devices may be increased by decreasing separations between electrodes as well as altering the chemical environment of the electrode-confined polymer. These very small, specific, sensitive devices provide means for interfacing electrical and chemical systems while consuming very little power.

3 Claims, 14 Drawing Sheets

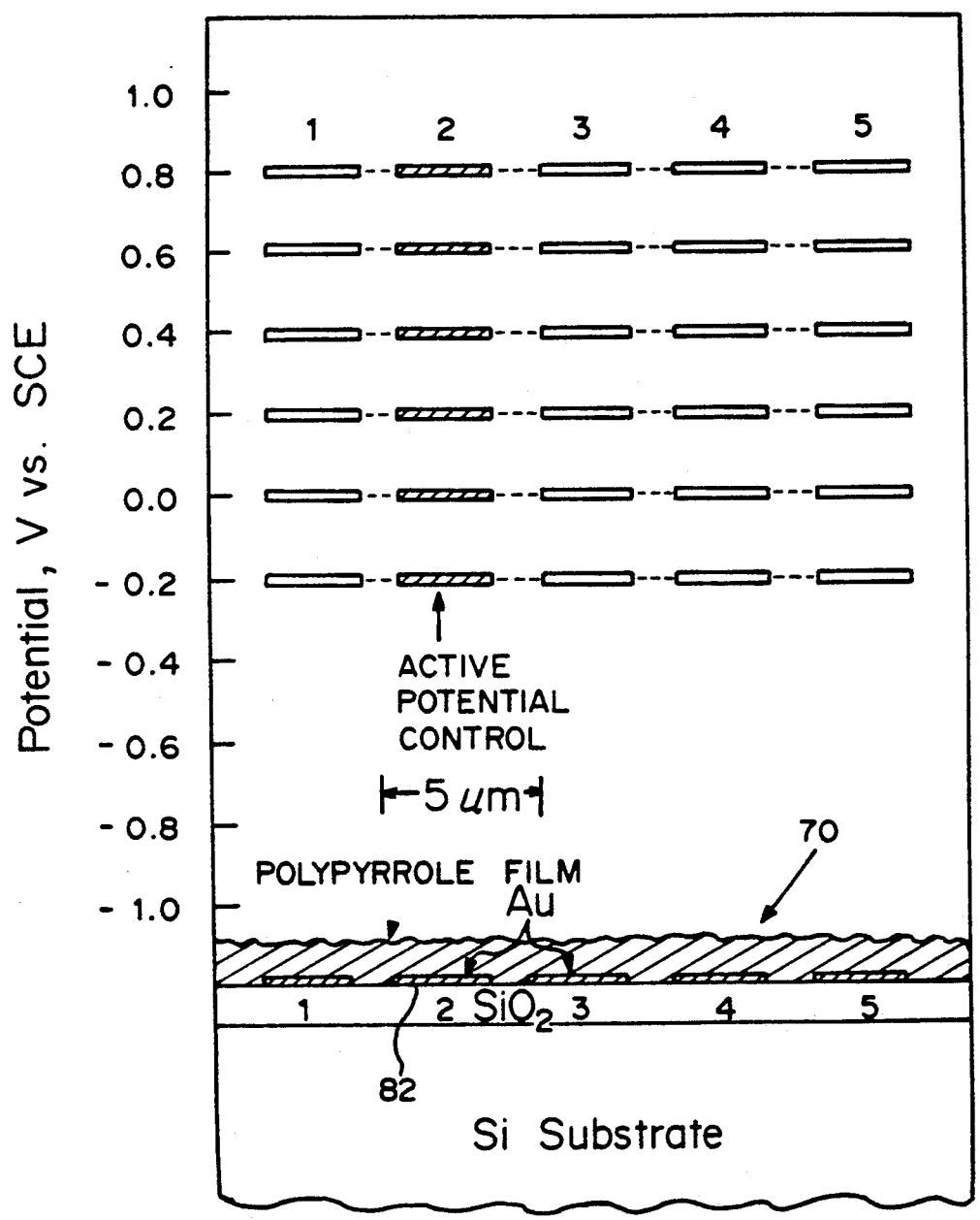

MOLECULE-BASED MICROELECTRONIC DEVICES

BACKGROUND OF THE INVENTION

The U.S. government has rights in this invention by virtue of Contract No. N0014-75-C-0880 and Contract No. N00014-82-K-0737 from the Office of Naval Research.

This is a continuation of U.S. Ser. No. 049,341, filed May 13, 1987, now U.S. Pat. No. 4,895,705, which is a divisional of U.S. Ser. No. 674,410 entitled "Molecule-Based Microelectronic Devices" filed Nov. 23, 1984 by Mark S. Wrighton, Henry S. White, Jr., and Gregg P. Kittlesen, now U.S. Pat. No. 4,721,601, issued Jan. 26, 1988.

Presently available solid state microelectronic devices consist of microcircuits with discrete circuit elements such as monolithic integrated circuits, transistors, diodes, resistors, capacitors, transformers, and conductors mounted on an insulating substrate. Thin film hybrid microcircuits are formed by vapor deposition of conductors, such as copper and gold, and resistors, such as tantalum, nichrome, and tin oxide onto a passive or insulating substrate such as silicon dioxide. An exact conductor pattern is obtained by masking or photolithographic etching. The entire circuit is subsequently encased with an epoxy dip to protect against moisture and contamination.

Modern integrated circuit devices, even highly miniaturized very large scale integrated devices (VLSI), are responsive only to electrical signals. There is now considerable interest in interfacing microelectronic devices with chemical and biological systems and it is therefore highly desirable to provide a microelectronic device that is responsive to such chemical or biological inputs. Typical applications for these devices include sensing of changes in pH and molar concentrations of chemical compounds, oxygen, hydrogen, and enzyme substrate concentrations.

Applicant is not aware of any apparatus or system which allows a direct interface between a microelectronic device sensitive to chemical imputs and a microminiature electrical circuit. Devices have been made on a larger scale which are sensitive to chemical input. These devices include such well known apparatus as pH sensors. Work in this area has recently centered around the use of electroactive polymers, such as polypyrrole or polythiophene. These compounds change conductivity in response to changes in redox potential. Recently, a polymeric semiconductor field effect transistor has been disclosed in a Japanese patent, 58-114465. As described in this patent, polymers such as trans-polyacetylene, cis-polyacetylene, polypyrrole, and polyvinyl phenylene have been used as inexpensive substitutes for single crystal silicon or germanium in making a semiconductor field effect transistor. There is no recognition of the unique properties of these polymers in this patent and, in fact, the polymers are treated as semiconducting material even though the properties of the polymers are distinctly different from that of silicon or germanium. The polymers are used as substitutes for semiconducting materials sensitive to electrical signals for uses such as in memory storage. Disadvantages to the FET as disclosed are that it is unstable and has a short useful life.

It is therefore an object of the present invention to provide a process for producing microelectronic devices responsive to chemical input which can be incorporated into microelectronic systems which are responsive to electrical input.

A further object of the present invention is to provide a process for constructing molecule-based microelectronic devices on silicon substrates which can easily be integrated with solid state silicon devices for signal processing.

Still another object of the invention is to provide small, sensitive, and specific microelectronic devices with very low power requirements.

A further object of the invention is to provide diodes, transistors, sensors, surface energy storage elements, and light-emitting microelectrode devices which can be controlled by molecular-level changes in electroactive polymer components.

SUMMARY OF THE INVENTION

The present invention is a process for making microelectronic devices which can be controlled by molecular-level changes in electroactive polymer components. These devices are fabricated by functionalizing electrodes formed by deposition of metal on silicon dioxide substrates using conventional masking and phtolithography techniques with polymers whose physical properties change in response to chemical signals. The key features are the small dimension of the electrodes and the small spacing, in the range of less than five microns, between them.

In one embodiment, an analogue of a solid state transistor, wherein a transistor is defined as a material whose resistance can be adjusted by an electrical signal, is formed from an array of gold microelectrodes derivatized with a redox polymer such as polypyrrole. When polypyrrole is oxidized, it conducts an electrical current between the microelectrodes. As in a solid state transistor, the current between the two outer microelectrodes of the array can be varied as a function of the potential of the polymer electrically connecting the electrodes in a manner analagous to the "gate" of a transistor. As the potential is altered, the oxidation or reduction of the polypyrrole can be effected. This device amplifies the very small signal needed to turn the polypyrrole from its reduced and insulating state to its oxidized and conducting state. Further variations are possible using additional polymers with different redox potentials.

In a second embodiment, a diode is fabricated on a silicon dioxide-silicon substrate from an array of two or more microelectrodes separated from each other by a distance of 2 microns or less, individually functionalized with a chemically responsive polymer, such as a redox polymer. Examples of redox polymers are polypyrrole, poly-N-methylpyrrole, polythiphene, poly-3-methylthiophene, polyvinylferrocene, derivatized styrene and polyaniline. As many different polymers may be used as there are pairs of microelectrodes. Since the polymers respond at different potentials, each pair of electrodes can be effectively isolated from the other microelectrodes.

In yet another embodiment, a microelectronic device with transistor or "triode-like" properties is fabricated by deposition of polyaniline onto an array of two or more gold microelectrodes. Polyaniline, a redox polymer, has the unusual property of being insulating at an electrical potential, less than +0.1 V vs. SCE in aqueous 0.5M NaHS0$_4$, greater than 10$^6$ times more conducting at a slightly higher electrical potential, +0.4 V vs. SCE in 0.5M NaHSO$_4$, and insulating at a higher electrical potential, +0.7 V vs. SCE in 0.5M NaHSO$_4$. The exact potential at which the polyaniline is conducting or insulating is determined by the medium, the amount of polyaniline connecting the electrodes, and interactions with other polymers. This device is particularly useful as an electrical switch between a specific range of potentials or as a pH or other chemical sensor. The device may be further modified for use as an oxygen or hydrogen sensor by connecting the polyaniline to a noble metal electrode such as a platinum electrode or by dispersing particles of noble metals such as palladium into the polyaniline.

Other specific embodiments of the present invention include surface energy storage elements and light-emitting microelectrodes.

BRIEF DESCRIPTION OF THE DRAWINGS

FIG. 8b is a graph of the potential, V vs. SCE, of five gold microelectrodes connected with polypyrrole where only one electrode is under active potential control.

FIG. 12 (inset) is a cross-sectional view of a device fabricated from two polyaniline-coated gold microelectrodes wherein $V_D$ is the potential between one microelectrode "source" and another microelectrode "drain" at a fixed gate potential, $V_G$, controlled relative to an aqueous saturated calomel reference electrode (SCE).

FIG. 13 (inset) is a graph of $I_D$ versus time in hours when $V_D$ is at 20 mV, $V_G$ is at +0.3 V vs. SCE, and the electrolyte is 0.5M NaHSO$_4$ at pH 1.

DETAILED DESCRIPTION OF THE INVENTION

Figure 1:
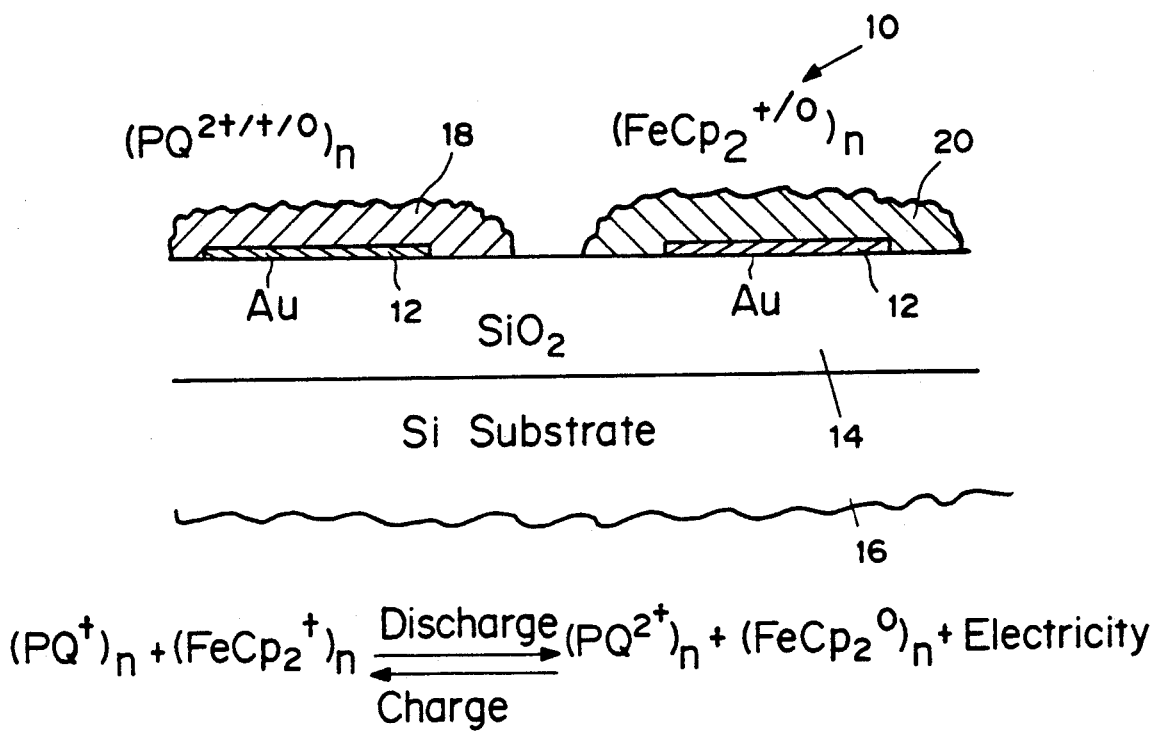
FIG. 1 is a cross-sectional view of a surface energy storage device wherein electrical energy is used to charge the device by reducing a polyviologen polymer, $(PQ^{2+/+})_n$, and oxidizing a polyvinylferrocene polymer, $(FeCp_2^{+/o})_n$.

The present invention is a process for producing molecule-based microelectronic devices consisting of two or more microelectrodes separated by a small dimension, which can be contacted individually and independently functionalized using electroactive polymers with specific properties that are responsive to chemical and/or electrical signals. Examples of one group of electroactive polymers are redox polymers which are insulating when reduced and conducting when oxidized.

The microelectrodes are small, typically on the order of 2 to 5 microns wide by 50 to 150 microns long by 0.1 to 0.15 microns thick, although even smaller electrodes may be utilized, and made of inert, electrically conductive material such as gold, silver, palladium, gold-platinum, and gold-palladium or other metals that are electrochemically inert. The conductor should be easily deposited and have low electrical resistance, good adhesion to the substrate, stability, and ability to be functionalized.

These electrodes are positioned on an inert substrate. An example of a preferred substrate would be oxidized silicon wafers made by growing a 4500 Angstroms to 10,000 Angstroms thick $SiO_2$ layer on <100> Si. Devices made according to the present invention on silicon wafers may be easily integrated into presently available solid state microelectronic devices, most of which are also produced on silicon wafers.

The small separation between electrodes, typically on the order of 0.1 to 2 microns, combined with the use of electroactive polymers with specific properties, is crucial to the invention. The smallest inter-electrode space technically feasible is preferred. The small inter-electrode space allows high current densities. As the distance between microelectrodes is increased, output decreases and "noise" increases. The direction of current flow, the ability to respond to a chemical signal such as a change in pH, the rate of response, the degree of response, the storage of energy, and the ability to place other pairs of electrodes in close proximity without interference is due to the choice, deposition, degree of separation and quantity of polymer.

Various groups of polymers known to those skilled in the art are suitable for use in the present invention. The requirements for such polymers are that they can be electrochemically deposited on individual electrodes and polymerized and that they can respond to a signal, in a reversible manner, in a way which can be electrochemically detected. Such materials are described by R. W. Murray in *Electroanalytical Chemistry*, Vol. 13, Edited by A. J. Bard (Marcel Dekker, N.Y., 1984).

Suitable electrochemically polymerizable materials for use in the present invention include redox polymers. Examples of such polymers are polypyrrole, polyaniline, poly-N-methylpyrrole, polythiophene, poly-3-methylthiophene and polyvinylferrocene (poly vinyl dicyclopentadienyliron). Styrene and vinyl aromatic derivatives such as vinyl pyridine, vinyl,2,2'-bipyridine and metal complexes of these derivatives, are also useful since they can be electrochemically polymerized and may be derivatized with a number of reagents, including biologically active agents such as enzymes and ionophores that complex with ions such as lithium and calcium.

Using two or more electrodes connected with one polymer, a transistor-like device may be fabricated. By choosing two or more polymers with different redox potentials, adjacent electrodes may be electronically isolated or made to function as diodes or surface energy storage units.

For polypyrrole and poly-N-methylpyrrole, the oxidized materials are electronic conductors. The conductivity varies by more than $10^{10}$ depending on the redox state of the polymers. The consequence of the very large difference in conductivity with redox state is that the potential drop can occur across a very small fraction of length of the connecting polymer when one microelectrode is held at a potential where the polymer is reduced and insulating and the other is held at a potential where the polymer is oxidized and conducting. For example, polypyrrole is insulating at approximately $-0.4$ V vs. SCE potential but becomes conducting at positive potentials up to any positive potential at which the polypyrrole is durable. The actual conductivities of the oxidized polymers, measured in $CH_3CH/0.1M$ [n-$Bu_4N]ClO_4$, of polypyrrole and poly-N-methylpyrrole, respectively, are approximately $10^{-2}$ ohm$^{-1}$·cm$^{-1}$ and $10^{-4}$ to $10^{-5}$ ohm$^{-1}$·cm$^{-1}$.

In contrast to polypyrrole, polyaniline can be made conducting by either a positive or a negative shift of the electrochemical potential, since polyaniline is essentially insulating at sufficiently netative (negative of 0.0 V vs. SCE) or positive (positive of $+0.7$ V vs. SCE) electrochemical potentials. As a result, a polyaniline-based device responds to a signal in a significantly different way from solid state transistors where the current passing between source and drain, $I_D$, at a given source to drain voltage, $V_D$, does not decrease with increasing gate voltage, $V_G$. The conductivity of polyaniline has been measured to span eight orders of magnitude and is sensitive to pH and other chemical parameters.

The potential at which a polymer exhibits a sharp change in conductivity due to oxidation is the threshold potential, $V_T$. $V_T$ can be manipulated by using different monomers or different redox polymers, and by varying the medium to be "seen" by the polymer.

Other polymers which are useful in the present invention include redox polymers known to be electrochromic materials, compounds which change color as a result of electrochemical reactions. Examples of such materials are polyvinylferrocene, polynitrostyrene, and viologens. Viologens, described by Wrighton et al in U.S. Pat. Nos. 4,473,695 and 4,439,302, the teachings of which are incorporated herein, are compounds formed from 4,4'-bipyridinium which may be polymerized and covalently bonded or otherwise confined to the surfaces of electrodes. Viologens such as dialkyl-4,4'-bipyridinium di-cation and associated anions, dichloride, dibromide, or di-iodide, form contrasting colors when oxidized or reduced. Since each monomer unit of viologen has a $2+$ charge which is balanced in the presence of two halide counter ions, the counter ions can be replaced with a complex ion such as $PtCl_6^{2-}$ which can then be reduced to yield embedded elemental Pt(O) in highly dispersed form. An enzyme such as hydrogenase can also be immobilized onto or throughout the redox polymer to equilibrate the redox polymer with the enzyme substrates.

Substituted viologens are useful for photogeneration of hydrogen from aqueous electrolytes, for reduction of metal-containing macromolecules, and on p-type silicon photocathodes in electrolytic cells.

The invention is further illustrated by the following non-limiting examples. Devices in these examples were constructed according to the procedure outlined below, with minor variations.

FABRICATION OF MICROELECTRODE ARRAYS

Microelectrode arrays were fabricated in the Massachusetts Institute of Technology Microelectronics Laboratory in the Center for Materials Science and Engineering which includes a class 100 clean room and is equipped to meet the specialized requirements for the production of solid state microelectronic devices such as "silicon chips".

A two-mask process was designed. The first mask was made for a metal lift-off procedure to form microelectrodes, leads, and contact pads. The second mask was made to pattern a photoresist overlayer leaving a 50 to 140 micron length of the microelectrodes and the contact pads exposed.

A microelectrode array was designed using the Computer Aided Design Program HPEDIT at a Hewlett Packard Model 2648A graphics terminal on a DEC-20. The design file was translated into Caltech Intermediate Form (CIF). This CIF file was translated to Mann compatible code and written on magnetic tape. Masks for photolithography were made from the file on magnetic tape using a Gyrex Model 1005A Pattern Generator. E-K 5"×5"×0.009" Extra Flat high resolution glass emulsion plates were used to make the photolithography masks. The emulsion plates were developed by a dark field process.

p-Si wafers of <100> orientation, two inches in diameter and 0.011 inches thick, obtained from Wacker Corp. were used as substrates upon which to fabricate the microelectrode arrays. The silicon wafers were RCA cleaned in a laminar air flow hood in the class 100 clean room. The wafers were immersed in hot aqueous 6% by volume $H_2O_2$/14% by volume aqueous $NH_3$, briefly etched in hydrofluoric acid diluted 10:1 with deionized water, immersed in hot aqueous 6% by volume $H_2O_2$/14% by volume HCl, rinsed in deionized water (resistance greater than 14 Mohm·cm), and spun dry. The cleaned wafers were loaded immediately into an oxidation tube furnace at 1100° C. under $N_2$. For examples 1 to 5, a dry/wet/dry/anneal oxidation cycle was used to grow a thermal oxide layer 4500 Angstroms thick. For example 6, a dry oxidation cycle was used to grow a thermal oxide 11850 Angstroms thick. Oxide thicknesses were measured using a Gaertner Model L117 ellipsometer. The oxidized wafers were taken immediately to the photolithography stage.

Each oxidized wafer was flood-coated with hexamethyldisilazane and spun at 6000 rpm for 20 sec. For examples 1 to 5, one ml of MacDermid Ultramac PR-914 positive photoresist was syringed onto each wafer. The wafer coated with resist was spun for 30 sec at 4000 rpm and then prebaked 35 min at 90° C. For example 6, one ml of Shipley 1470 positive photoresist was syringed onto each wafer and the wafer spun for 30 seconds at 6000 rpm. The coated wafer was then prebaked 25 minutes at 90° C.

A GCA Mann 4800 DSW Wafer Stepper was used to expose the photoresist. The Mann uses the 405 nm line of a 350 W Hg arc lamp as a light source. The mask image is reduced 5:1 in the projection printing. For examples 1 to 5, an exposure time of 0.850 sec was used and the photoresist developed 60 sec in MacDermid Ultramac MF-62 diluted 1:1 with deionized water. For example 6, the wafer was exposed for 1.2 seconds and developed 60 seconds in Shipley 312 developer diluted 1:1 with dionized water. The developed wafers were then cleaned in a planar oxygen etching chamber at 75–100 W forward power in 20 mtorr of oxygen for 15 seconds.

A bilayer metallization was performed. A MRC 8620 Sputtering System was used in preparing the microelectrode arrays of examples 1 to 5. The bilayer metallization of the wafers used in example 6 was performed in a NRC 3117 electron beam evaporation system. Wafers were placed on a quartz plate that was freshly coated with chromium. The wafers were backsputtered 2 min at 50 W forward power in an argon plasma at 5 mtorr. Chromium was sputtered at 50 W forward power to produce a layer of chromium. The layer on the wafers in examples 1 to 5 was 200 Angstroms thick. The layer in example 6 was 50 Angstroms thick. Gold was then sputtered at 50 W forward power to produce a layer 1000 Angstroms thick. Chromium serves as an adhesion layer for the gold. The combined chromium/gold thickness of the wafers used in example 6 was measured to be 1052 Angstroms on a Dektak II surface profile measuring device.

At this point, the chromium/gold was in direct contact with the $SiO_2$ substrate only in the areas that were to form the microelectrodes, leads, and contact pads and on photoresist in all other areas. The chromium/gold on photoresist was removed by a lift-off procedure: the metallized wafers were immersed in warm acetone, in which soft-baked positive photoresist is soluble, for 75 minutes for the wafers used in examples 1 to 5 and 5 minutes for the wafers used in example 6. The wafers used in examples 1 to 5 were briefly sonicated in acetone to remove the metal between microelectrodes, dried, and then cleaned of residual photoresist in a planar oxygen plasma etching chamber at 200 W forward power in 50 mtorr oxygen for 60 sec.

The wafers used in example 6 was blasted with acetone from a Paasche air brush with $N_2$ at 70 psi, sonicated for 30 minutes in acetone, then rinsed with acetone and methanol before drying. The wafers were then cleaned in a mixture of hot aqueous 6% by volume $H_2O_2$/14% by volume aqueous $NH_3$, rinsed in deionized water (greater than 14 megaohm.cm), and spun dry. The wafers were then baked at 180° C. for 40 minutes before repeating the photoresist spin coating process. The wafers were again prebaked at 90° C. for 25 minutes and then exposed in a Karl Suss America Inc. Model 505 aligner for 11 seconds, using a dark field mask. The photoresist was developed in Shipley 312 developer diluted 1:1 with deionized water to expose the bond pads and the array of microelectrode wires. The exposed areas were cleaned of residual photoresist in the oxygen plasma etching chamber at 75–100 W for 1 minute. The remaining photoresist was hardbaked at 180° C. for 15 hours.

Wafers were then baked at 180° C. for 40 minutes before repeating the photoresist spin coating process. The wafers were again prebaked at 90° C. for 25 minutes and then exposed in a Karl Suss America Inc. Model 505 aligner for 11 seconds, using a dark field mask. The photoresist was developed in Shipley 312 developer diluted 1:1 with deionized water to expose the bond pads and the array of microelectrode wires. The exposed areas were cleaned of residual photoresist in the oxygen plasma etching chamber at 75–100 W for 1 minute. The remaining photoresist was hard baked at 180° C. for 15 hours.

Individual die (chips) were scribed and separated. The chips were mounted on TO-5 headers from Texas Instruments with Epoxi-Patch 0151 Clear from Hysol Corp. A Mech-El Ind. Model NU-827 Au ball ultrasonic wire bonder was used to make wire bonds from the chip to the TO-5 header. The leads, bonding pads, wire bonds, and header were encapsulated with Epoxi-Patch 0151. The header was connected through a TO-5 socket to external wires. The external wires were encased in a glass tube. The header was sealed at the distal end of the glass tube with heat shrink tubing and Epoxi-Patch 1C white epoxy from Hysol Corp.

Prior to use as a microelectrode array, the array was tested to establish the leakage current between the various electrodes of the array. Arrays characterized as usable have a measured resistance between any two electrodes of greater than $10^9$ ohms in non-aqueous electrolyte solution containing no added electroactive species. In many cases only a fraction of the electrodes of an array were usable. Prior to use in experimentation the microelectrode arrays were tested further in aqueous electrolyte solution containing 0.01M $K_3[Fe(CN)_6]$ and 0.01M $K_4[Fe(CN)_6]$ or with $[Ru(NH_3)_6]Cl_3$ to establish that the microelectrodes give the expected response. Typically, a negative potential excursion to evolve $H_2$ cleaned the gold surface sufficiently to give good electrochemical response to the $Fe(CN)_6^{3-/4-}$ or $Ru(NH_3)_6^{3+/2+}$ redox couples. The electrolyte used for electrical measurement was 0.1M $NaClO_4$ in $H_2O$ solvent, 0.5M $NaHSO_4$, or 0.1M $[n-Bu_4N]ClO_4$ in $CH_3CN$ solvent.

ELECTROCHEMICAL EQUIPMENT

Most of the electrochemical experimentation in examples 1 to 5 was carried out using a Pine Model RDE 3 bipotentiostat and potential programmer. In cases where two microelectrodes were under active potential control and a third was to be probed, a PAR Model 363 potentiostat/galvanostat was used in conjunction with the Pine Model RDE 3. All potentials were controlled relative to an aqueous saturated calomel reference electrode (SCE). Typically, electrochemical measurements were carried out under $N_2$ or Ar at 25° C.

For example 6, most of the electrochemical experimentation was carried out using a Pine Model RDE 4 bipotentiostat and potential programmer. In some cases where only a single potentiostat was needed a PAR Model 173 potentiostat/galvanostat and a PAR Model 175 universal programmer was used. Potential step experiments were carried out using the RDE 4 with a Tektronix type 564B storage oscilloscope as the recorder.

DERIVATIZATION OF MICROELECTRODES

In examples 1 to 5, the gold microelectrodes were functionalized by oxidation of 25-50 mM pyrrole or N-methylpyrrole in $CH_3CN/0.1M$ $[n-Bu_4N]ClO_4$. The polypyrrole was deposited at $+0.8$ V vs. SCE, and the poly-N-methylpyrrole was deposited at $+1.2$ vs. SCE. The deposition of the polymer can be effected in a controlled manner by removing the array from the derivatization solution after passing a certain amount of charge. Electrodes were then examined by cyclic voltammetry in $CH_3CN/0.1M$ $[n-Bu_4N]ClO_4$ to assess the coverage of polymer and to determine whether the polymer coated two or more electrodes resulting in a "connection" between them.

Prior to use as a microlectrode array, each microelectrode wire in the devices used in example 6 was tested with an ohmmeter to make sure it was not shorted to any other wire on the device. Then each microelectrode was tested by running a cyclic voltammogram in 0.01M $Ru(NH_3)_6^{3+}/0.1M$ $NaNO_3/H_2O$. The microelectrodes were derivatized by oxidation of a stirred 0.44M aniline solution in 0.5M $NaHSO_4/H_2O$ at pH 1. The polyaniline was deposited at $+0.9$ V vs. SCE. Electrodes were then examined by cyclic voltammetry in 0.5M $NaHSO_4$ at pH 1 to assess the coverage of polymer and to determine whether the polymer coated two or more electrodes resulting in a connection between them. Macroscopic gold electrodes were derivatized with polyaniline by the same procedure to accurately relate the thickness of polyaniline to cyclic voltammetry response and the charge passed in the anodic deposition. Typically, a portion of the gold flag was covered with grease prior to depositing the polyaniline over the exposed gold surface. The grease was then removed with $CH_2Cl_2$ to give a well defined step from gold to polyaniline.

EXAMPLE 1

In one embodiment of the present invention, depicted in FIG. 1, a surface energy storage device 10 is constructed from two gold microelectrodes 12, 3 microns wide by 140 microns long by 0.12 microns thick, deposited on a 1 micron thick $SiO_2$ insulator 14 grown on a <100> Si substrate 16 and separated by a distance of 1.4 microns. Each microelectrode is individually coated with electrochemically deposited and polymerized polymers, polyviologen 18 and polyvinylferrocene 20. Electrical energy can be used to charge the device by reducing the polyviologen, the $(PQ^{2+})_n$ polymer, and oxidizing the polyvinylferrocene, the $(FeCp_2^0)_n$ polymer, according to the following reaction:

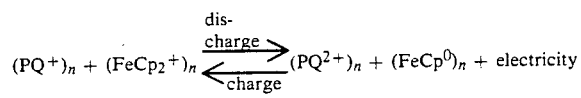

$$(PQ^+)_n + (FeCp_2^+)_n \underset{\text{charge}}{\overset{\text{discharge}}{\rightleftharpoons}} (PQ^{2+})_n + (FeCp^0)_n + \text{electricity}$$

EXAMPLE 2

Figure 2:
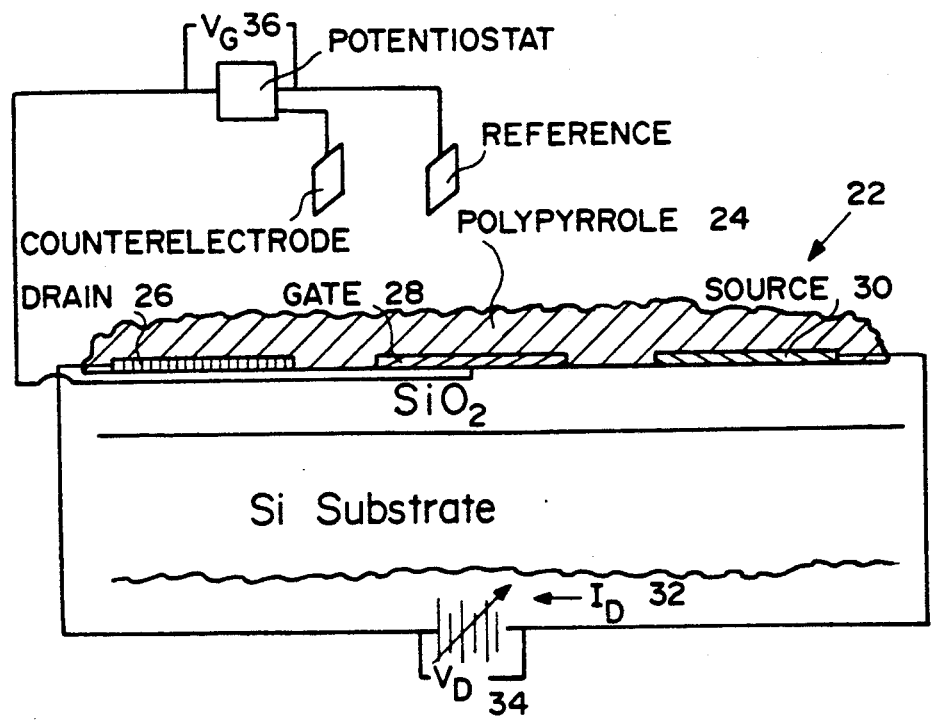
FIG. 2 is a cross-sectional view of a molecule-based transistor consisting of three gold microelectrodes, derivatized with polypyrrole and immersed in electrolyte, with a schematic showing how the electrical potential of the gate is set using a potentiostat with a counter electrode and a saturated calomel reference electrode (SCE).

In another embodiment of the present invention, shown in FIG. 2, a molecule-based transistor 22 is fabricated from three gold microelectrodes separated by 1.4 microns, derivatized with polypyrrole 24. Typical coverage of the polypyrrole is $10^{-7}$ mol/cm$^2$ of exposed gold, and the individual microelectrodes are electrically connected. The microelectrodes are wired so as to correspond to the drain 26, gate 28, and source 30 as in a conventional solid state transistor.

Figure 3:
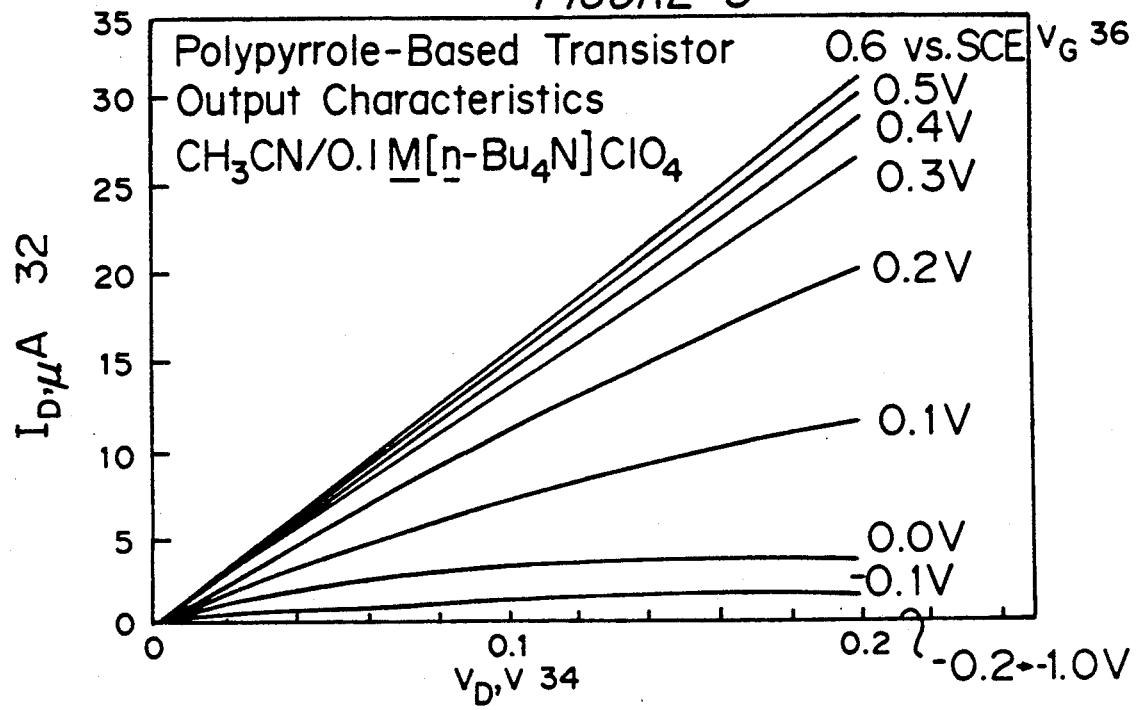
FIG. 3 is a graph showing the output characteristics of the transistor of FIG. 2 as $I_D$, the current between source and drain, as a function of $V_D$, the potential between source and drain, at various fixed gate potentials, $V_G$.

The properties of the device are characterized by immersing the device in an electrolyte, $CH_3CN/0.1M$ $[n-Bu_4N]ClO_4$, and measuring the current 32 between source 30 and drain 26, $I_D$, as a function of the potential 34 between source and drain, $V_D$, at various fixed gate potentials 36, $V_G$. The results are shown in FIG. 3.

At values for $V_D$ of less than 0.5 V, the device is "off" when $V_G$ is held at a negative potential where the polypyrrole is expected to be insulating and $I_D$ is small. When $V_G$ is moved to potentials more positive than the oxidation potential of polypyrrole, approximately $-0.2$ V vs. SCE, the device "turns on" and a significant steady-state value for $I_D$ can be observed for modest values of $V_D$. The close spacing of the microelectrodes allows an easily measurable current to pass between the source 30 and the drain 26 when $V_D$ is significant and $V_G$ is above the threshold, $V_T$. $V_T$, the gate potential at which the device starts to turn on, is approximately equal to the redox potential of polypyrrole. For $V_G$ more positive than $V_T$, the value of $I_D$ increases at a given value of $V_D$, in a manner consistent with the increasing conductivity due to an increasing degree of oxidation. At sufficiently positive values of $V_G$, greater than or equal to $+0.5$ V vs. SCE, $I_D$ becomes insensitive to further positive movement of $V_G$ at a given value of $V_D$, a result consistent with measurements of the resistance of the oxidized polypyrrole coated on a microelectrode array. A small range of $V_D$ values (0 to 0.2 V) is used to minimize electrochemical reactions at the source 30/polymer 24 and drain 26/polymer 24 interfaces.

A fraction of $10^{-8}$C of charge is required to obtain the maximum steady-state value of $I_D$ when $V_D$ is equal to 0.2 V with this device. The value of $I_D$ achievable with the device is $4\times 10^{-5}$ C/s. It is apparent from these results that a small signal to the gate microelectrode can be amplified in much the same way that a small electrical signal can be amplified with a solid state transistor. The major difference is that the turn on/turn off time in the molecule-based system is dependent on the rate of a chemical reaction rather than on electron transit times across the source to drain distance. For the molecule-based system, the properties such as $V_T$ and minimum turn on signal can be adjusted with rational variation in the monomer used to prepare the polymer. Use of smaller dimensions and materials other than polypyrrole can also lead to faster switching times.

EXAMPLE 3

Figure 4A:
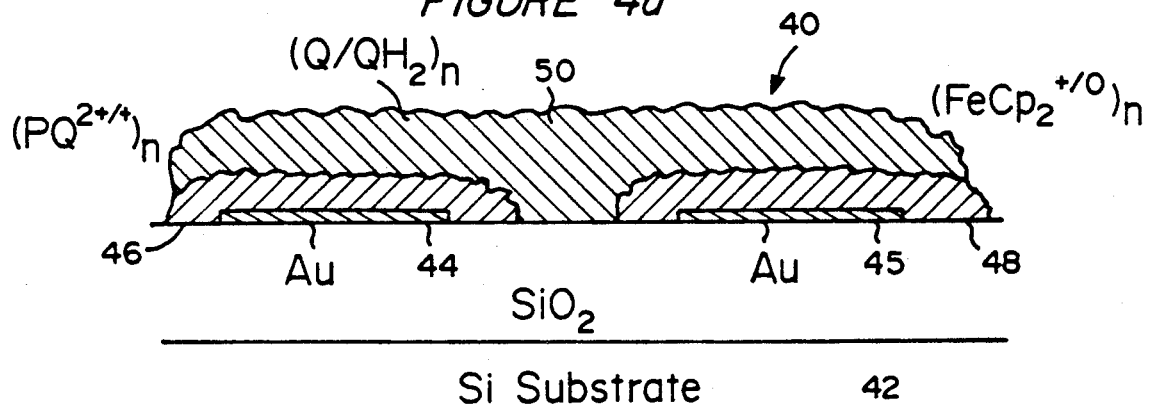
FIG. 4a is a cross-sectional view of a molecule-based transistor, consisting of two gold electrodes coated with polyvinylferrocene, $(FeCp_2^{+/o})_n$, and polyviologen, $(PQ^{2+/+})_n$, and functionalized with a quinone-based polymer, $(Q/QH_2)_n$, having a pH-dependent redox potential which is more negative or positive than the potential of th viologen polymer, depending on the pH.

As shown in FIG. 4a, a molecule-based pH sensor 40 can theoretically be fabricated using a two microelectode array on a $SiO_2$-Si substrate 42.

The two gold microelectrodes 44, 45 are coated with polyviologen 46, $(PQ^{2+/+})_n$, and polyvinylferrocene 48, $(FeCp_2^{+/o})_n$, respectively, and then overlaid with another polymer 50 with a different pH dependent redox potential, such as a polyquinone, $(Q/QH_2)_n$, whose redox potential is above the redox potential of the polyviologen at high pH and between that of the polyviologen and polyvinylferrocene at low pH.

Figure 4B:
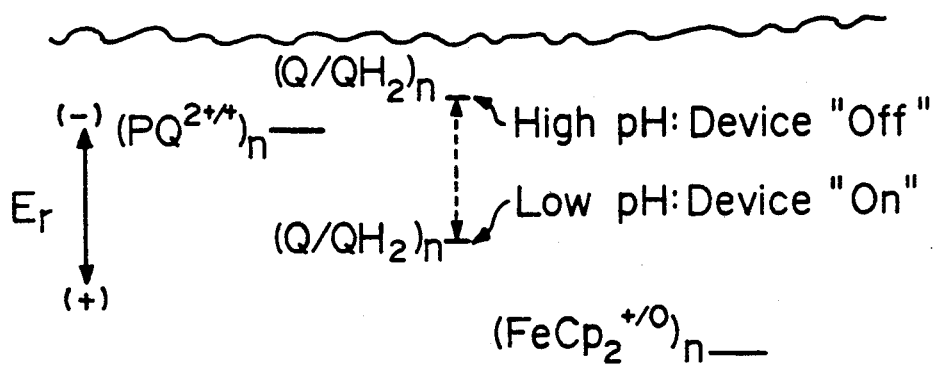
FIG. 4b is a schematic of the effect of pH variation on the polymers in the transistor of FIG. 4a and shows the approximate relationship of the redox potentials.

The pH variation serves as the signal to be amplified. Varying the pH results in a variation in current passing between the two gold electrodes at a fixed potential difference with the negative lead to the viologen coated electrode. As shown by FIG. 4b, alteration of the pH changes the redox potential of polymer 50. Low pH acts to make it easier to reduce polymer 50. Current can flow between source 44 and drain 45 when the negative lead is attached to the polyviologen-coated gold microelectrode 44 and the positive lead is connected to the polyvinylferrocene-coated gold microelectrode 45 and the redox potential of the polyquinone is between the redox potentials of the two polymers 46 and 50 coating source 44 and drain 45. At a fixed potential difference, the current passing between the two microelectrodes 44 and 45 should depend on the pH of the solution contacting the polymer 50.

A pH sensor may also be fabricated by coating a microelectrode array with a polymer such as polyaniline. For a device consisting of two gold microelectrodes, 0.1 micron thick, 4.4 microns wide, and 50 microns long, separated by a distance of 1.7 microns, coated with a layer of polyaniline approximately 5 microns thick, changes in the pH of the surrounding medium markedly alter the conductivity. For example, the value of $I_D$ at $V_D$ equal to 20 mV and $V_G$ of 0.2 V vs. SCE is reduced upon raising the pH of the solution, where $I_D$ is the current between one electrode and the next, $V_D$ is the potential between the first and second electrode, and $V_G$ is the potential between the two electrodes and a saturated calomel reference electrode. $I_D$ at pH 1 is approximately $10^2$ times greater than at pH 6.

Polyaniline is limited to use with solutions of pH less than 6 to preclude irreversible chemical changes that occur at the higher pH values. However, other pH-sensitive redox polymers may be used to fabricate microelectrode pH-sensors for other pH ranges.

Numerous uses in chemical systems are possible for such sensing devices. For example, such a device may be used to detect subtle changes in pH of aqueous solutions. Electrical signals generated by the device could be directly amplified and processed further.

EXAMPLE 4

Figure 5:
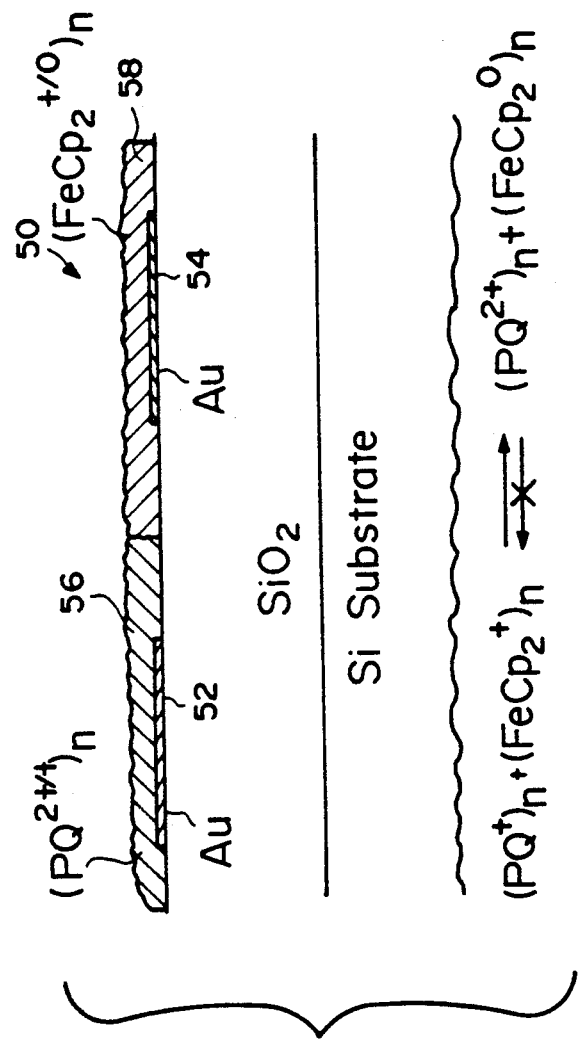
FIG. 5 is a cross-sectional view of a molecule-based diode consisting of two gold microelectrodes derivatized with two polymers of different redox potentials.

A molecule-based diode 50, produced according to the present invention, is shown in FIG. 5. Microelectrodes 52 and 54 are each individually covered with polymers 56 and 58 having very different redox potentials. The current passes between the two heavily coated, connected microelectrodes 52 and 54 as a function of the threshold potential of the diode, which is dependent on the redox potentials of the polymers. Electrons only flow from microelectrode 52 to microelectrode 54 due to the large difference in the redox potentials of the two polymers 56 and 58. For example, for a polyviologen/polyvinylferrocene diode, charge will pass only when the negative lead of the applied potential is connected to the gold electrode 52 coated with polyviologen 56 and the positive lead is attached to the gold electrode 54 coated with polyvinylferrocene 58. This reaction is shown as:

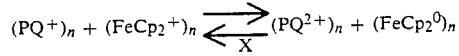

Figure 6:
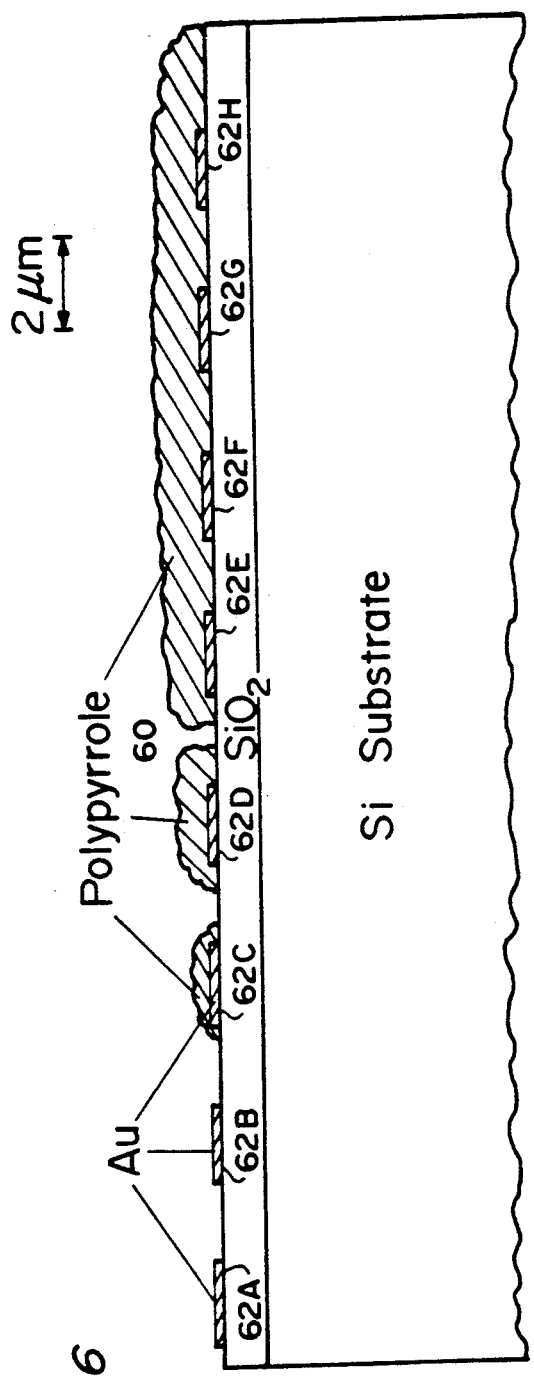
FIG. 6 is a cross-sectional view of an array of eight gold microelectrodes derivatized with different amounts of polypyrrole.

As shown in FIG. 6, it is possible to electrochemically deposit electroactive polymers 60 on individual electrodes 62a–h in variable amounts. The electrodes 62e–h which are bridged by the polymer 60 are electrically connected: charge can pass from one microelectrode 62e to another microelectrode 62f–h via conduction mechanisms of the polymer 60. Connected electrodes are typically associated with coverages of approximately $10^{-7}$ mol polymer/$cm^2$ electrode. Addressing one electrode oxidizes and reduces the polymer 60 over all of the electrodes 62e–h.

Figure 7:
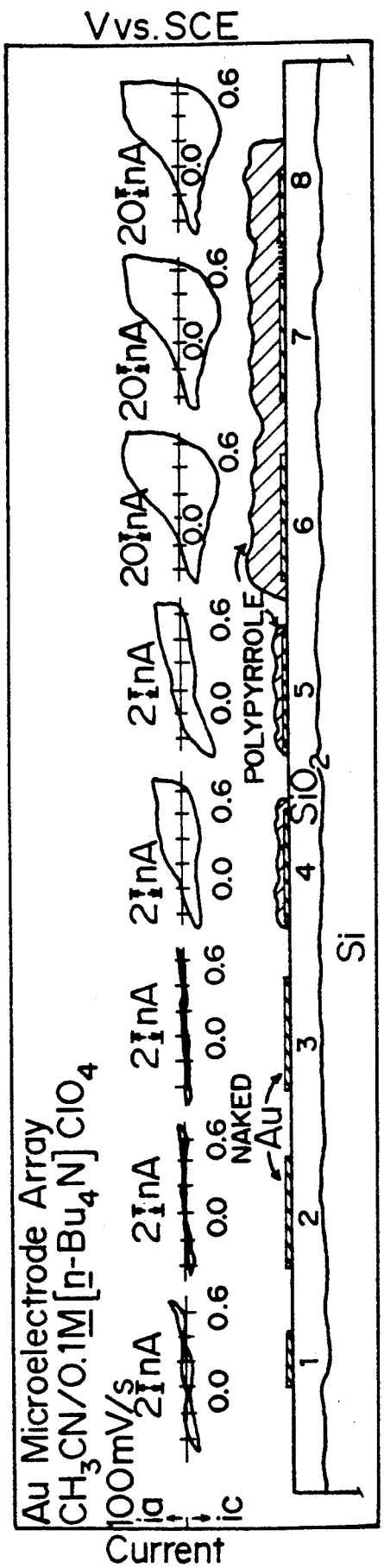
FIG. 7 is a graph of cyclic voltammograms at 100 mV/s for an array like that in FIG. 6 in CH$_3$CN/0.1M [n-Bu$_4$N]ClO$_4$. The bottom portion of the sketch is the expected result based on the derivatization procedure and electrochemical response.

FIG. 7 shows the cyclic voltammetry of the polypyrrole modified array of FIG. 6 in $CH_3CN/0.1M$ [n-$Bu_4$]-$ClO_4$ containing no added redox active species. The unfunctionalized electrodes 62a, 62b, and the electrode 62c, with a negligible amount of polypyrrole, lack the cyclic voltammetry signal characteristic of an electrode-confined polymer. Immediately adjacent to the non-derivatized electrodes 62a–c are electrodes 62d–h that show cyclic voltammograms characteristic of electrode-confined polypyrrole. The shape of the voltammogram is nearly the same as for a macroscopic gold electrode derivatized in the same manner. In addition, the potential of the oxidation and reduction peaks are as expected for the oxidation and reduction of polypyrrole.

Based on the integration of the charge passed upon cycling the derivatized microelectrodes 62 individually between the negative and positive limits, it can be seen that controlled amounts of polypyrrole 60 can be deposited on the electrodes 62. The same results, with the expected differences in the oxidation and reduction potentials, were shown using poly-N-methylpyrrole instead of polypyrrole.

Figure 8A:
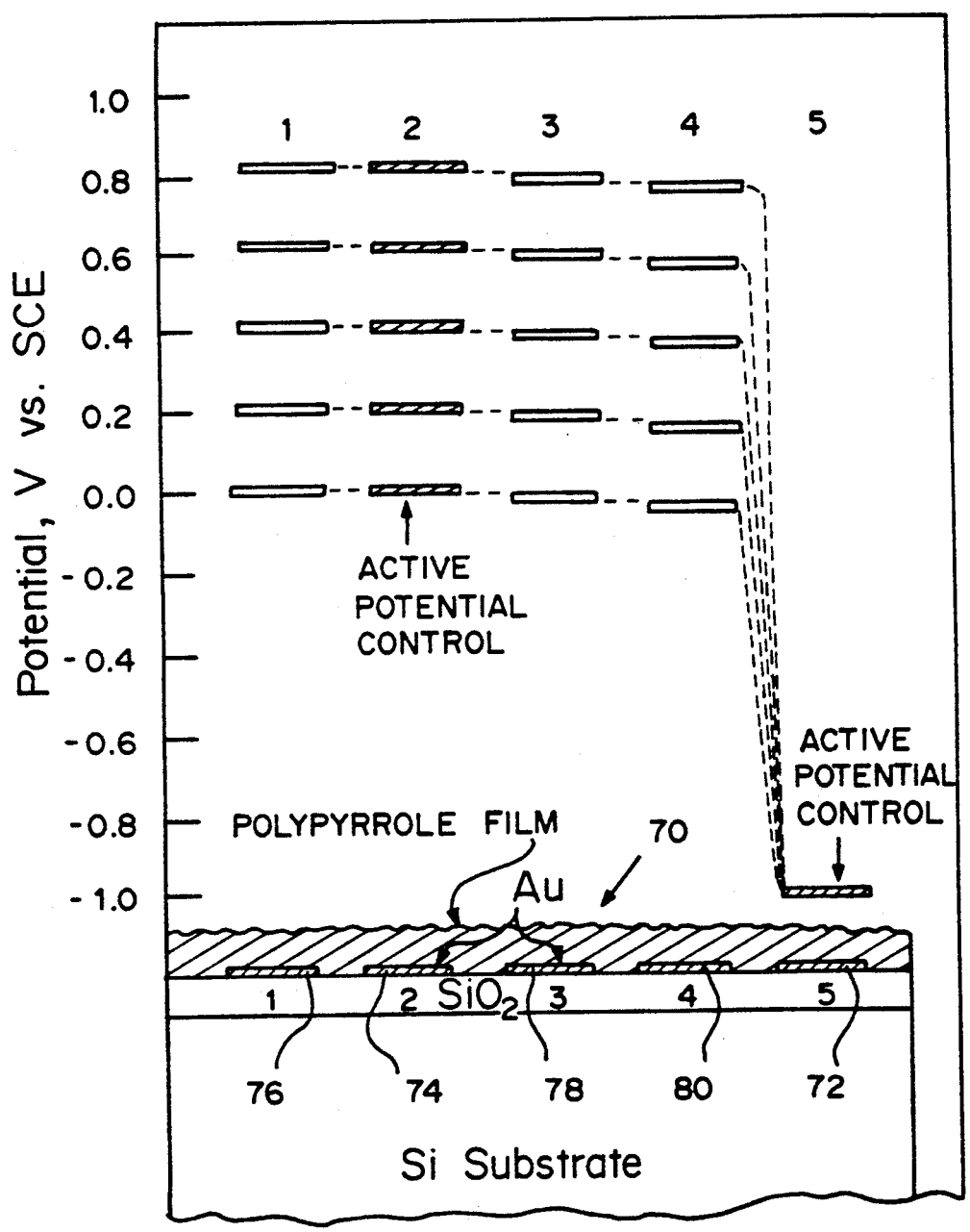
FIG. 8a is a graph of the potential, V vs. SCE, measured in CH$_3$CN/0.1M [n-Bu$_4$N]ClO$_4$, of five gold microelectrodes connected with polypyrrole when one is under active potential control at −1.0 V vs. SCE and one is at a positive potential at which the polypyrrole is expected to be conducting.

FIG. 8a and 8b show the spatial potential distributions across a polypyrrole array 70 where one (FIG. 8b)

or two (FIG. 8a) of the electrodes is under active potential control. The entire array 70 was immersed in CH$_3$CN/0.1M [n-Bu$_4$]ClO$_4$ and a biopotentiostat used to actively control the potential of one (FIG. 8b) or two (FIG. 8a) microelectrodes against a common reference and counter electrode in the electrolyte solution.

The potential of one microelectrode 72 in the five electrode array 70 was set at a negative potential of $-1.0$ V vs. SCE and the potential of another microelectrode 74 varied between 0.0 and 1.0 V vs. SCE.

As shown in FIG. 8a, the potentials of electrodes 76, 78, and 80 not under active potential control are nearly equal to the positive potential applied to electrode 74. Although a small potential drop of approximately 50 mV occurs over the 9 micron distance separating electrodes 74 and 80, the essential finding is that nearly all, up to 1.8 V, of the potential drop occurs across a narrow region immediately adjacent to electrode 72 under active potential control at $-1.0$ V vs. SCE. The result is consistent with the difference in conductivity between the reduced and oxidized state of the polypyrrole, of which the consequence is that the potential drop occurs across a very small fraction of length of the connecting polymer when one microelectrode is held at a potential where the polymer is reduced and insulating and another is held at a potential where the polymer is oxidized and conducting. This would not be an expected result for a polymer with only a moderate conductivity, such as those that exhibit redox conductivity where a linear change in concentration of redox centers across the thickness spanned by two electrodes at differing potentials would give a potential profile predicted by the Nernst equation.

FIG. 8b shows that when only one 82 of the microelectrodes is under active potential control in the positive region, all of the electrodes are at the same potential as would be expected when there is an electrical connection between them. When one of the microelectrodes is driven to a negative potential, it would be expected that all would ultimately follow. Upon reduction, however, the polymer becomes insulating and the rate of potential following can be expected to be slower.

Figure 9:
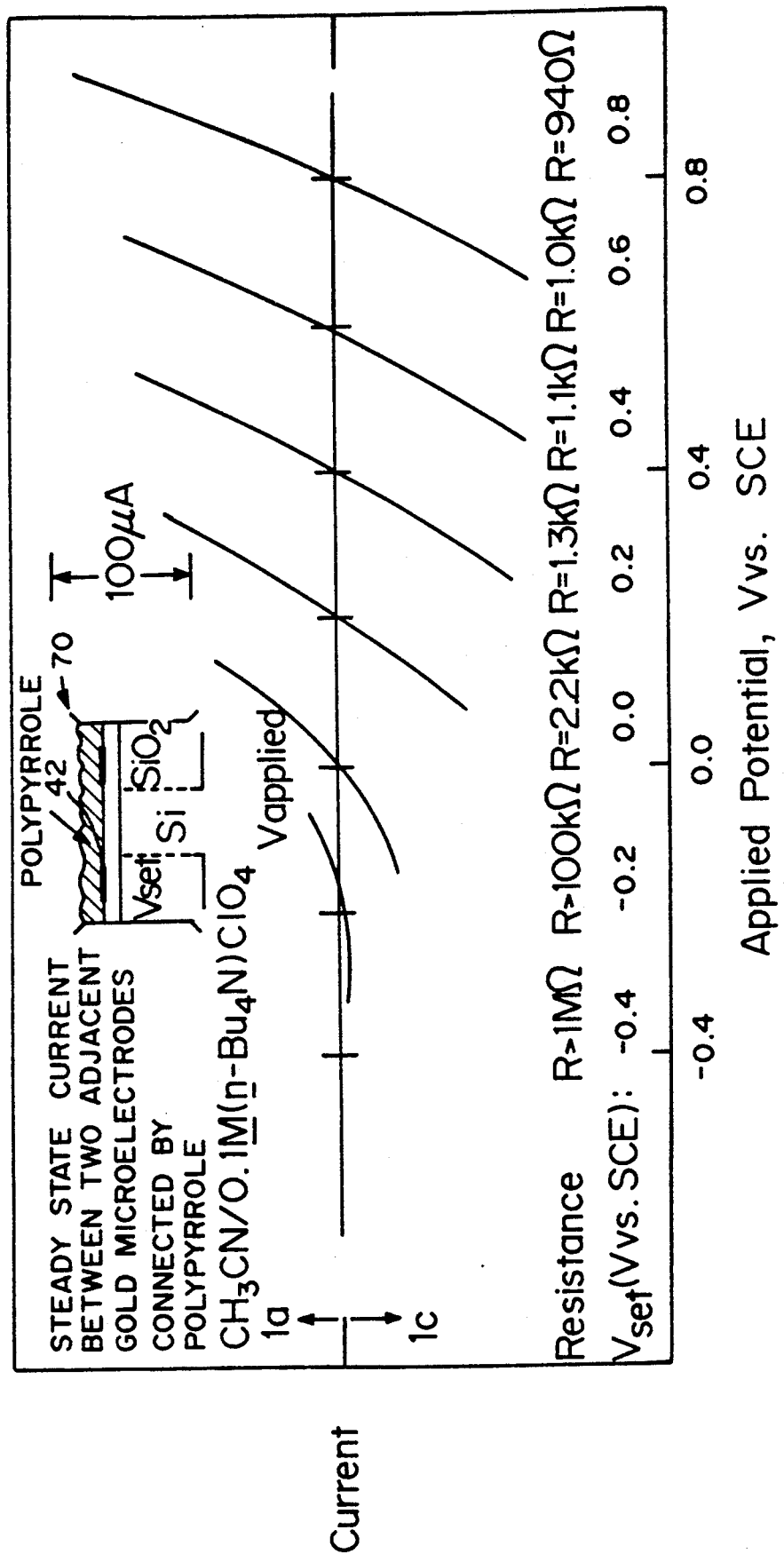
FIG. 9 is a graph of the current, i, measured between electrodes, versus applied potential, $V_{appl}$ vs. SCE, for two adjacent microelectrodes connected with polypyrrole as a function of $V_{set}$, where $V_{set}$ is the fixed potential vs. SCE of one of the two electrodes, and $V_{appl}$, where $V_{appl}$ is the potential of the other electrode.

As shown by the current vs. potential data in FIG. 9, polypyrrole connected-microelectrodes 90 behave in a diode-like fashion. Current vs. $V_{applied}$ curves are shown as a function of the potential, $V_{set}$, at which one 92 of the electrodes is fixed relative to the SCE. The current measured is that passing between the two microelectrodes. The magnitude of the current passing through one microelectrode is identical to that passing through the other microelectrode but opposite in sign.

Figure 10A:
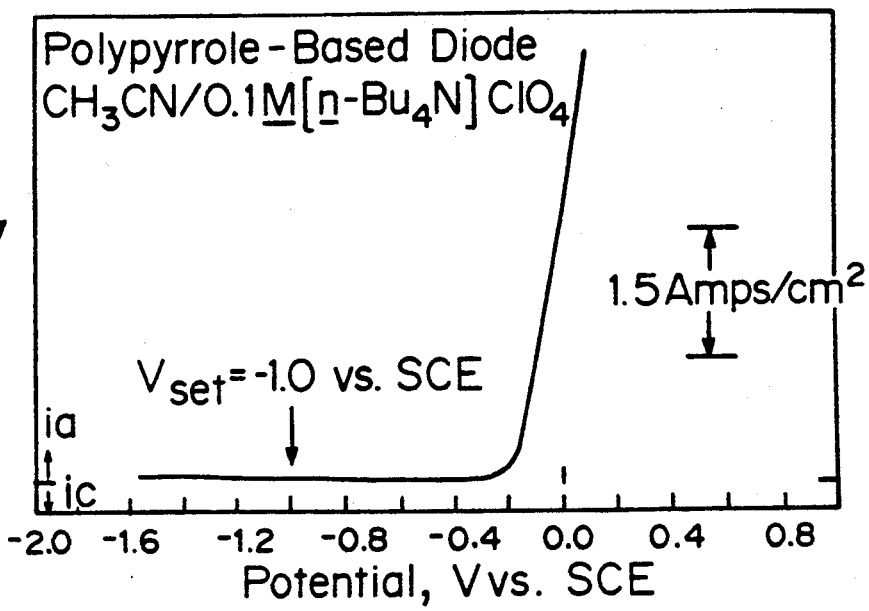
FIG. 10 is a graph comparing the diode characteristics for two microelectrodes connected with (a) polypyrrole and (b) poly-N-methylpyrrole where the fixed potential, $V_{set}$, in (a) is +1.0 V vs. SCE and in (b) is −0.6 V vs. SCE.

When $V_{set}$ is sufficiently positive, the current vs. $V_{applied}$ curve is linear over a wide range of $V_{applied}$. The resistance of polypyrrole from the slope of such plots is about $10^3$ ohms. Current densities exceeding 1 kA/cm$^2$ were observed. When $V_{set}$ is sufficiently negative, there is a broad range of the current vs. $V_{applied}$ curve where there is insignificant current. Therefore, as shown in FIG. 10a, a good diode characteristic can be obtained using polypyrrole coated, closely spaced microelectrodes. The onset of current closely corresponds to the situation where the $V_{appl.}$ results in the conversion of the polypyrrole from its reduced and insulating state to its oxidized and strongly conducting state.

Figure 10B:
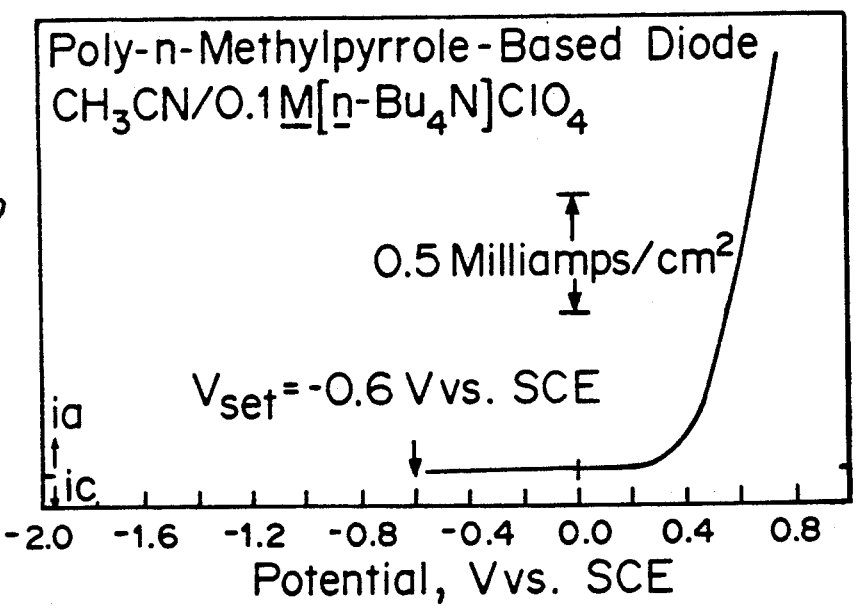

As shown in FIG. 10b, results using poly-N-methylpyrrole in place of polypyrrole in the array shown in FIG. 9 were similar except that the value of $V_{set}$ necessary to obtain a current that is linear as $V_{applied}$ is varied is more positive than with polypyrrole. The resistance of the poly-N-methylpyrrole is $10^5$ to $10^6$ ohms. Both the higher resistance and the more positive potential necessary to obtain the conducting regime are consistent with the known differences between polypyrrole and poly-N-methylpyrrole.

EXAMPLE 5

Figure 11:
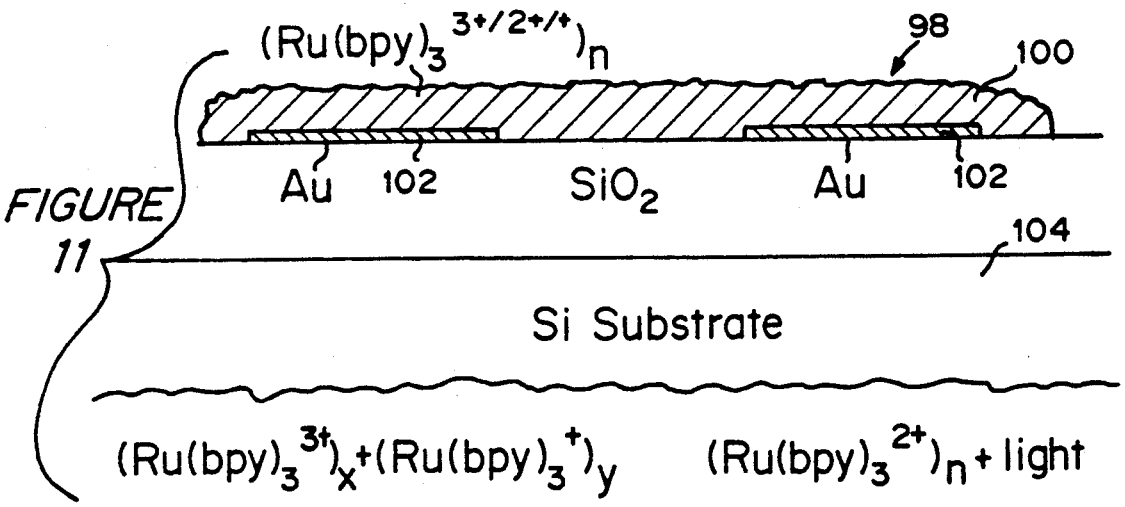
FIG. 11 is a cross-sectional view of a light-emitting pair of microelectrodes wherein the two gold microelectrodes are connected by a polymer such that application of a voltage, approximately 2.6 V, results in emission of light characteristic of an excited tris, 2,2-bipyridine ruthenium (II) complex, Ru(bpy)$_3^{2+}$.

A light emitting device 98 may also be made according to the process of the present invention. As shown in FIG. 11, light is emitted from a polymer 100 overlaying two gold microelectrodes 102 on a silicon dioxide-silicon substrate 104 when an electrical current is applied. In the depicted device, light characteristic of an excited Ru(bpy)$_3^{2+}$ species is emitted when a voltage of approximately 2.6 V is applied.

Polymers useful in a light emitting device according to the present invention can be polymerized from any monomers which are electrochemiluminescent, such as vinyl derivatives of rubrene or diphenyl anthracene.

EXAMPLE 6

A triode-like device was also constructed by electrochemical deposition and oxidation of a polyaniline film onto a microelectrode array consisting of eight gold electrodes, 0.1 micron thick, 4.4 microns wide, and 50 microns long, each individually addressable and separated from each other by 1.7 microns.

The magnitude of the current passing between electrically connected microelectrodes at a given applied potential depends on the electrochemical potential of the polyaniline. In an electrolyte of aqueous 0.5M NaHSO$_4$, the current at a fixed applied potential is maximum at an electrochemical potential of $+0.4$ V vs. SCE and declines by a factor of greater than $10^6$ upon reduction to a potential of $+0.1$ V vs. SCE or oxidation to $+0.7$ V vs. SCE.

The polyaniline-functionalized microelectrodes were examined by cyclic voltammetry in 0.5M NaHSO$_4$ at pH 1 to assess coverage of the polymer and to determine whether the polymer coating two or more electrodes results in an electrical connection between them. Derivatization of the electrode can be controlled by adjusting the amount of polyaniline by varying the amount of charge passed in the electrochemical polymerization. At one extreme, the amount of polyaniline can be small enough to derivatize the individual microelectrodes but not to electrically connect them. At the other extreme, polyaniline can be deposited in amounts sufficient to electrically connect all of the microelectrodes.

Both a separate, unconnected microelectrode and multiple, connected electrodes show the same cyclic voltammogram at 50 mV/s in 0.5M NaHSO$_4$ as does a single unconnected reference microelectrode at 50 mV/s in 0.5M NaHSO$_4$. This is consistent with one electrode being capable of oxidizing all of the polyaniline present on a single microelectrode or on multiple connected microelectrodes. When adjacent derivatized microelectrodes are not connected, the sum of the areas under the cyclic voltammograms for the individual electrodes is the area found when the microelectrodes are externally connected together and driven as a single electrode. The thickness of polyaniline is not measured to be directly proportional to the integrated cyclic voltammetry wave as it is for surface-confined, viologen derived polymers. This lack of direct proportionality may be attributable to morphological changes in the polymer with increasing thickness.

As shown in FIG. 12 (inset), a triode-like device 110 was constructed by coating two adjacent gold microelectrodes 112, 114 with a five to 10 micron thick electrochemically deposited and polymerized film of polyaniline 116. Measurements were made by immersing the device 110 in aqueous 0.5M $NaHSO_4$ at 25° C. under an inert atmosphere of $N_2$ or Ar. Devices constructed in this manner exhibit fairly long term stability.

Figure 13:
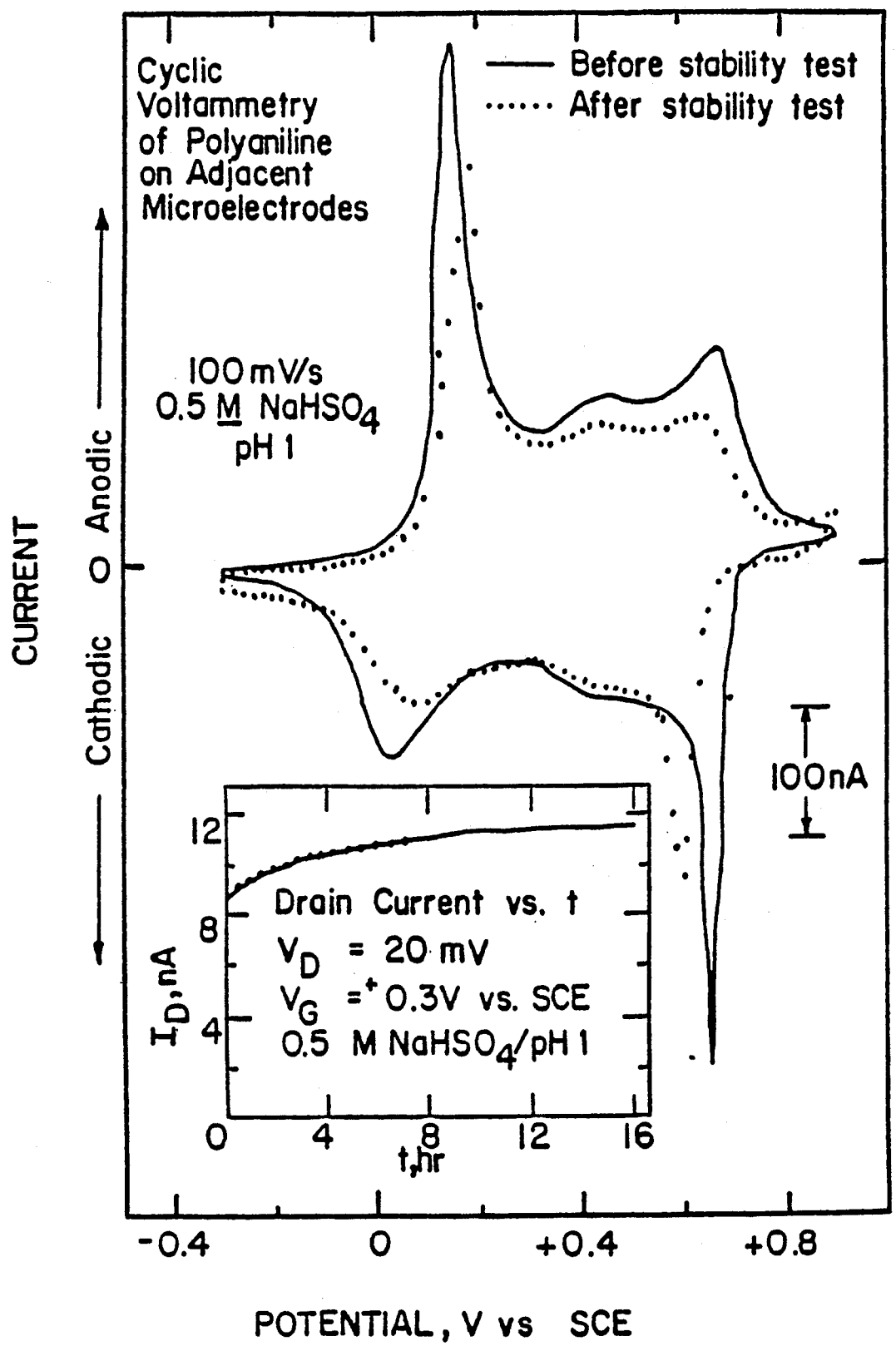
FIG. 13 is a graph of a cyclic voltammogram at 100 mV/s for a device such as the one described in FIG. 12 (inset) when $V_G$ is +0.3 V vs. SCE and $V_D$ is 20 mV. . . . . is at 0 hours and . . . is after 16 hours.

As shown by the cyclic voltammogram in FIG. 13 for the device 110, the connected pair of electrodes exhibits a nearly constant steady state current between the two microelectrodes for at least 16 hours when $V_D$ is 20 mV and $V_G$ is 0.3 V vs. SCE. In general, devices can be used for characterization for several days without significant deterioration.

Figure 14A:
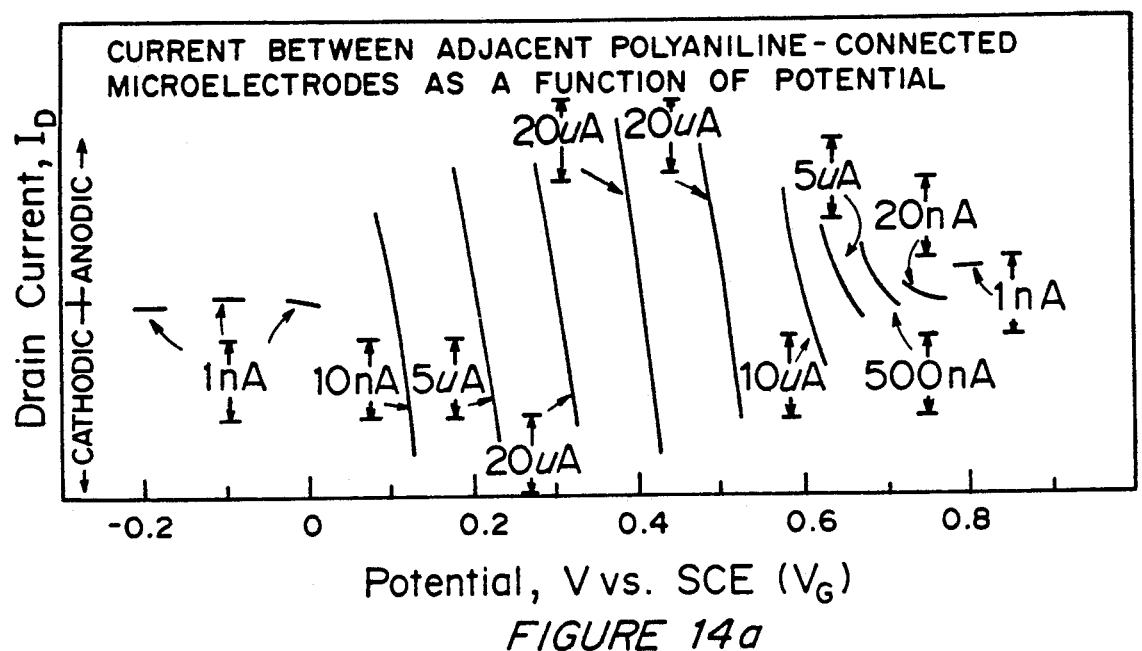
FIG. 14a is a graph of the $I_D$ vs. $V_G$ for a device such as the one shown in FIG. 12 (inset), where $V_G$ is varied from −0.2 V vs. SCE to +0.8 V vs SCE.
Figure 14B:
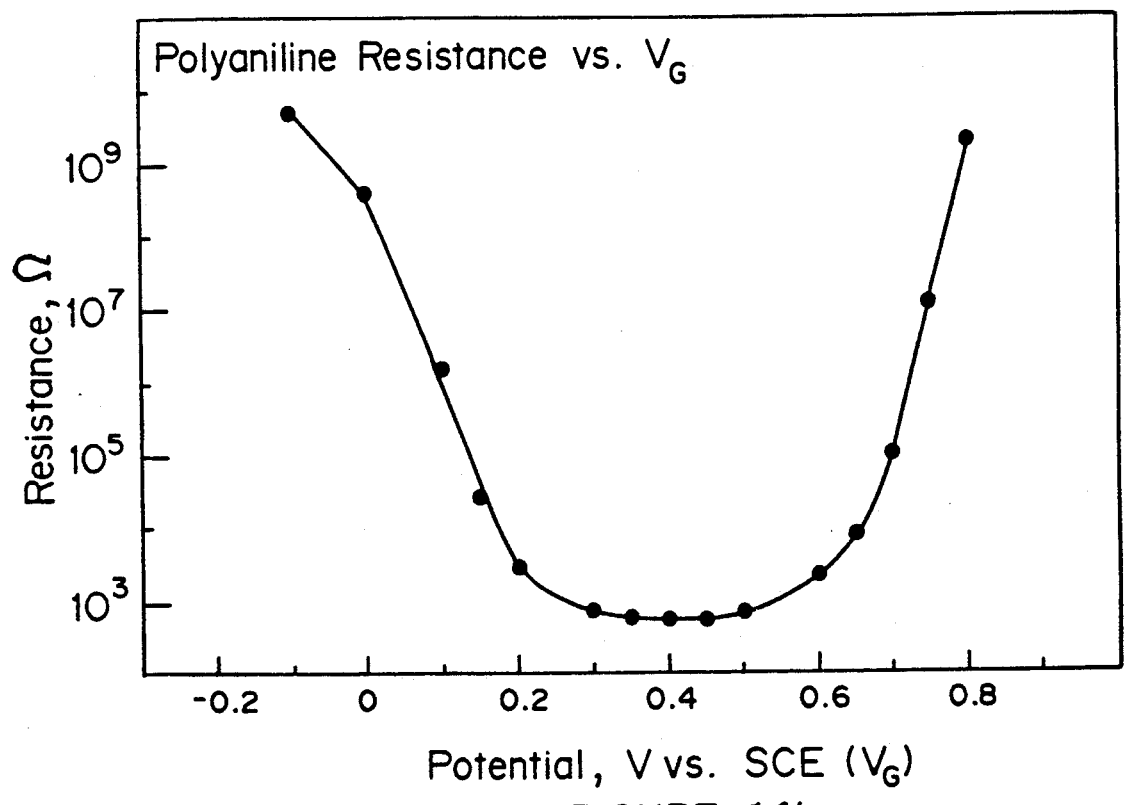
FIG. 14b is a graph of resistance in ohms versus $V_G$ for a device such as the one in FIG. 12 (inset).

The conductivity of polyaniline which is immersed in an electrolyte such as aquous 0.5M $NaHSO_4$ depends on the electrochemical potential, which can be varied by varying $V_G$. As shown in FIGS. 14a and 14b, the resistance of polyaniline depends on its electrochemical potential. The minium resistance is at an electrochemical potential in the vicinity of +0.4 V vs. SCE. Changes in resistance in excess of $10^6$ are routinely measured.

The minimum resistance for polyaniline is similiar to that for polypyrrole connecting two microelectrodes spaced 1.4 microns apart, as shown in example 3. It is significantly different from polypyrrole, however, in that polyaniline is less conducting at potentials less than or greater than +0.4 V vs. SCE. The change in resistance of polyaniline is essentially reversible for potentials less than +0.6 V vs. SCE. Potentials significantly more positive than +0.6 V vs. SCE yield an increase in the resistance of the polyaniline when the potential is again decreased to +0.4 V vs. SCE. The limit of positive applied potential is determined by $O_2$ evolution and limited durability of the polyaniline. The limit of negative applied potential is determined by the onset of $H_2$ evolution.

Figure 12A:
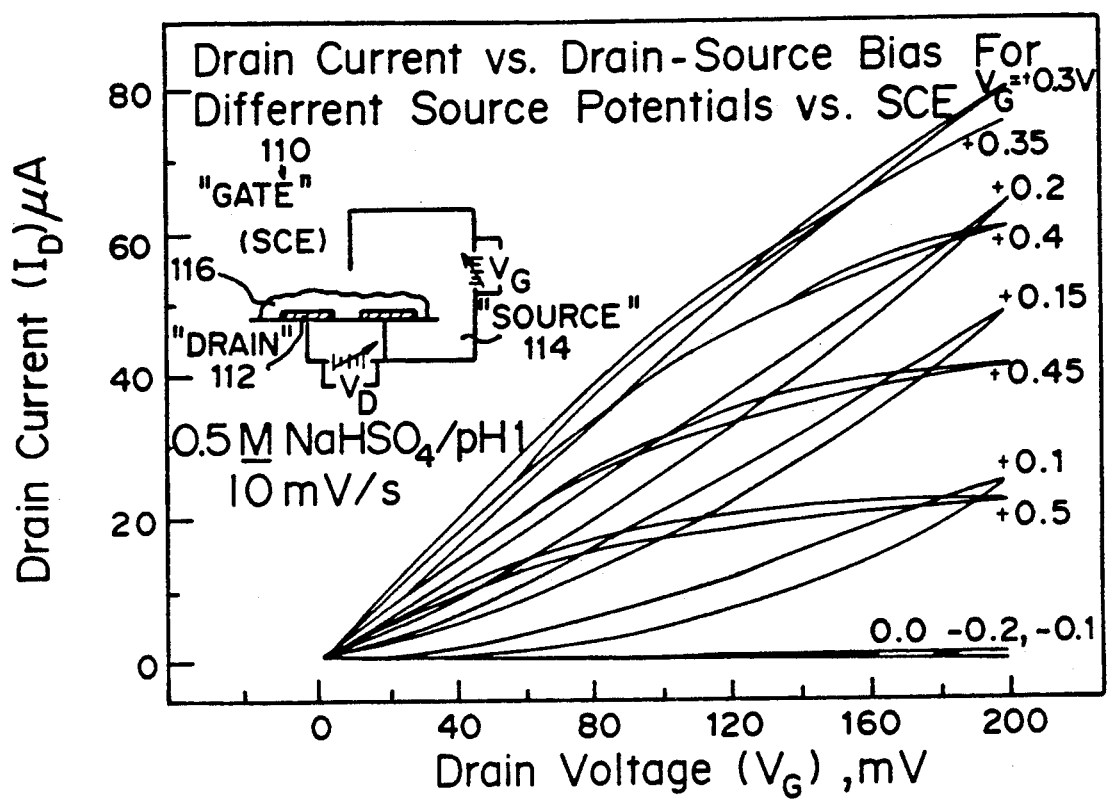
FIG. 12a is a graph of the drain current, $I_D$, in microamps versus the drain voltage, $V_D$, in mV for the device shown in the inset at various values of $V_G$, where the charge passed in setting the gate to a potential where there is conductivity between source and drain can be regarded as an input signal.
Figure 12B:
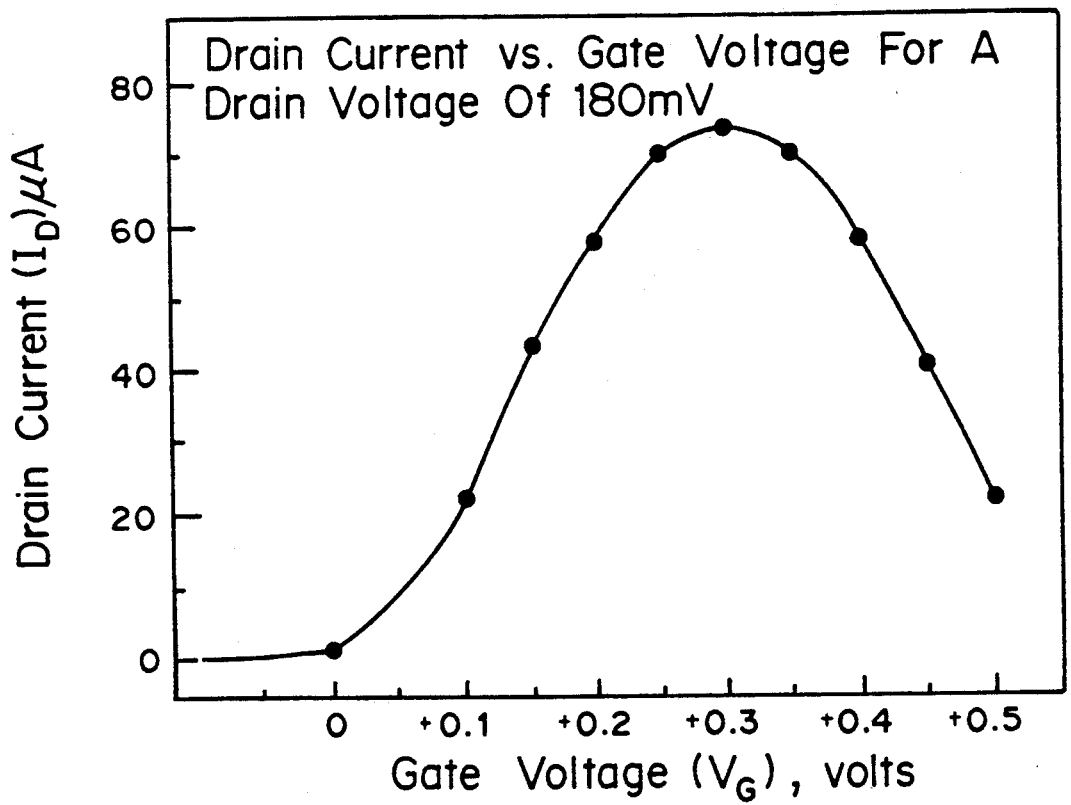
FIG. 12b is a graph of $I_D$ vs. $V_G$ at a fixed $V_D$ of 0.18 V for the device shown in the inset.

As shown in FIGS. 12a and 12b, the triode-like device 110 shows an increase and then a decrease in $I_D$ as $V_G$ is varied from negative to positive potentials, unlike conventional solid state devices which show an increase in $I_D$ as $V_G$ is varied until the $I_D$ ultimately levels off at a constant, $V_G$-independent value. The charge passed in setting the gate to a potential where there is conductivity between the source 114 and drain 112 can be regarded as an input signal. For the device 110, the charge necessary to completely turn on the device is approximately $10^{-6}$ C.

Transconductance, $g_m$, is determined by the equation:

$$\left. \frac{\partial I_D}{\partial V_G} \right|_{V_D} = g_m$$

Using the data in FIG. 12a and 12b, the maximum value of $g_m$ for device 110 is approximately 20 millisiemens per millimeter of gate width, as determined from the rising part of the $I_D$—$V_G$ curve as $V_G$ is moved to a potential more positive than approximately 0.1 mA/V.

By convention, gate length in $Si/SiO_2$/metal field effect transistors (MOSFET) is the separation of source and drain. "Width" therefore corresponds to the long dimension of the device 110. Since the $g_m$ of device 110 is only about one-order of magnitude less than that for good MOSFET devices, the signal from the polyaniline-based device can be fed to conventional MOSFET in the form of voltage across a load resistance for further amplification.

Figure 15:
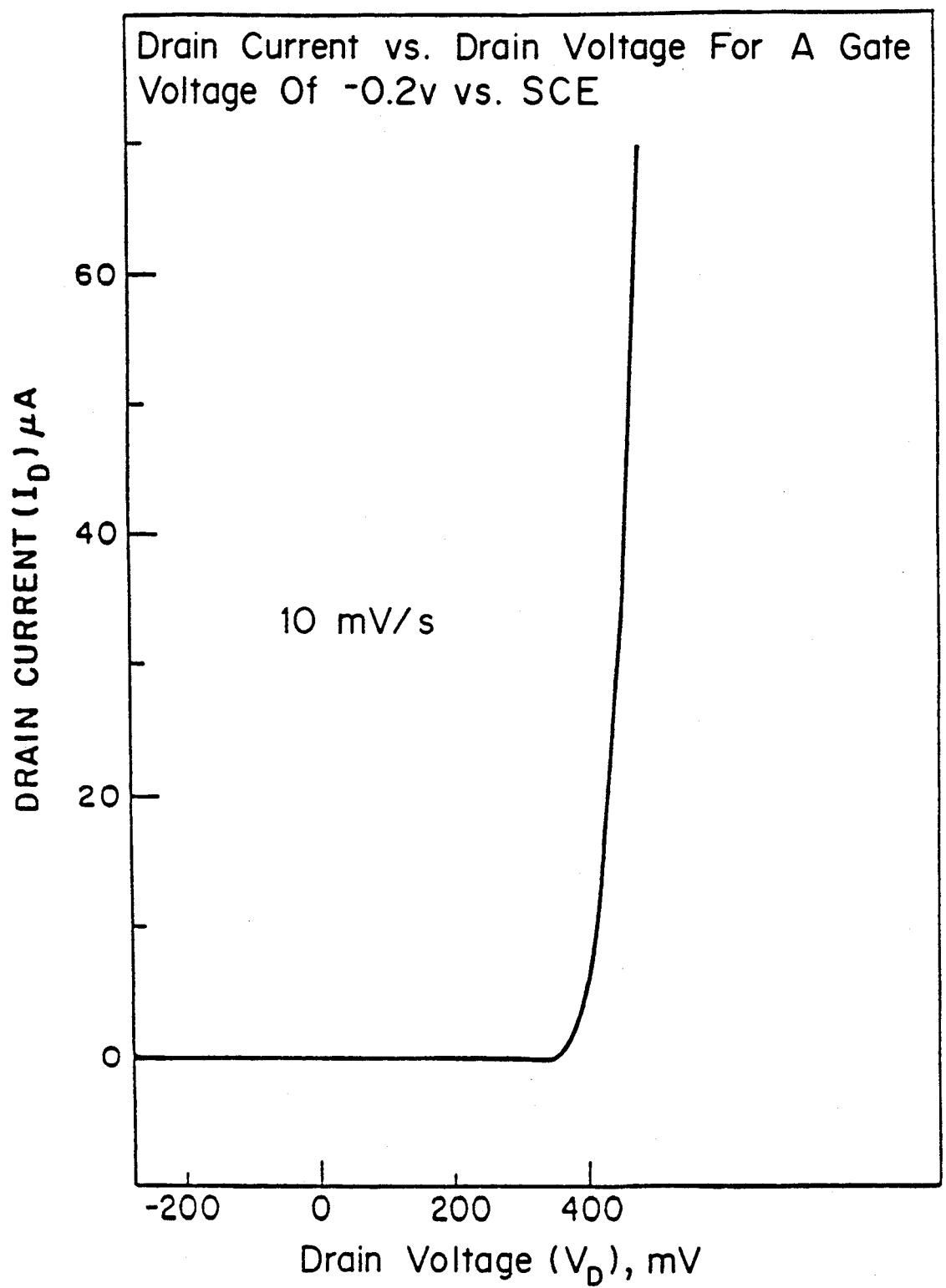
FIG. 15 is a graph for a device such as the one shown in FIG. 12 (inset) of $I_D$ in microamps versus $V_D$ in mV at a $V_G$ of −0.2 V vs. SCE, a potential at which polyaniline is reduced and insulating.

Diode-like behavior can be obtained using device 110, as shown in FIG. 15, at $V_G$ values where the polyaniline is reduced and insulating. Current passes between the microelectrodes 112 and 114 when the "source" microelectrode 114 is oxidized. If the "drain" microelectrode 112 is moved to the negative of the source 114, current does not flow because the polyaniline remains insulating. Device 110 is not an exact analogue of a solid state diode because it is not a two-terminal device as is a p-n junction or a metal/semiconductor Schottky barrier. The diode-like behavior of device 110 results from a chemical reaction of the polymer 116 at a particular potential that causes a change in conductivity of the polymer 116.

Persistent diode-like behavior is obtained by maintaining one microelectrode, the drain 112, at a negative potential at which it is insulating. Difficulties are encountered with degradation of the polyaniline when the potential of the microelectrode is held at a potential positive enough for the polyaniline to be insulating, +0.7 V vs. SCE, with the other microelectrode at a more negative potential.

Figure 16:
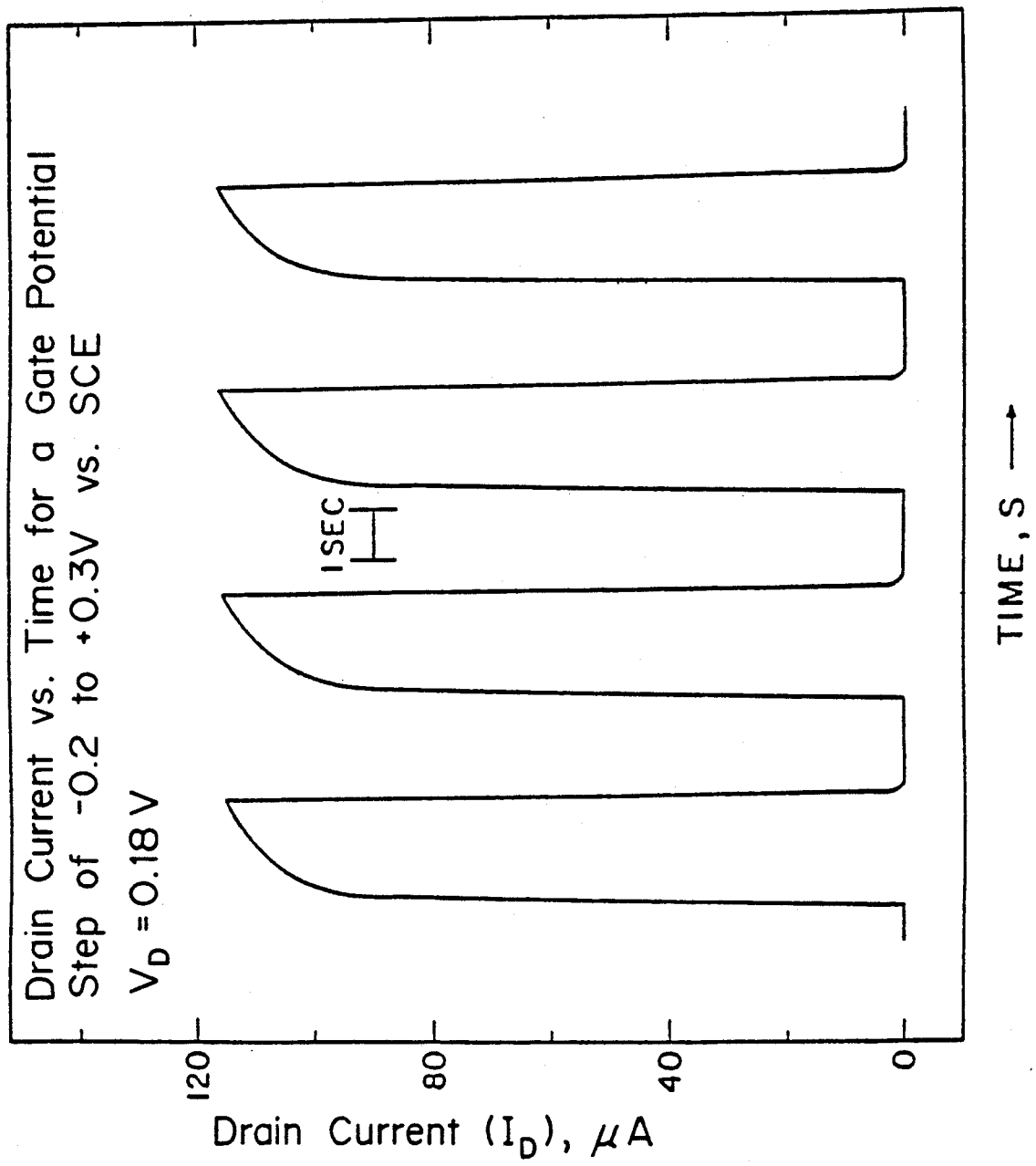
FIG. 16 is a graph of $I_D$ versus time in seconds at $V_D$ of 0.18 V for a device such as the one shown in FIG. 12 (inset) for a $V_G$ step of −0.2 to +0.3 V vs. SCE.

Chemical-based devices depend on chemical reactions such as redox reactions which occur relatively slowly compared to the turn on/turn off speeds for solid state diodes and transistors. As shown in FIG. 16, device 110 can be turned on and off in less than one second. In FIG. 16, the value of $I_D$ is shown for a potential step of $V_G$ from −0.2 to +0.3 V vs. SCE then back to −0.2 V vs. SCE at $V_D$ of 0.18 V. By monitoring the rise and fall of $I_D$ of the potential steps, on to off times of less than 50 ms and slightly longer off to on times were shown.

The polyaniline-coated device 110 exemplifies the type of molecule-based devices that could be used as chemical sensors where the input signal to the device is a redox agent that can equilibrate with the polyaniline 116 to change the value of $I_D$ at a given value of $V_D$. The specificity of the device stems from the fact that only those redox reagents that will bring the electrochemical potential of the polyaniline to a value that will allow current to pass will be detected. Further specificity arises from the failure of the polyaniline to react with a particular given redox reagent. For example, polyaniline does not equilibrate with the $H^+/H_2$ redox couple. There is, however, rapid equilibration of polyaniline with one-electron outer-sphere redox reagents such as $Ru(NH_3)_6^{3+/2+}$, $E^{o'}$ approximately equal to −0.18 V vs. SCE which is close to the $E^{o'}$ of $H^+/H_2$ at pH=1 of approximately −0.3 V vs. SCE.

Polyaniline also equilibrates with $Fe(CN)_6^{3-/4-}$. For example, immersion of the polyaniline-based device 110 into a solution of aqueous 0.5M $NaHSO_4$ containing the oxidant $K_3[Fe(CN)_6]$, $E^{o'}$ of $[Fe(CN)_6]^{3-/4-}$ approximately equal to +0.2 V vs. SCE, turns the device "on". Immersion of the device into a solution of 0.5M $NaHSO_4$ containing $Ru(NH_3)_6^{2+}$ turns the device "off".

Figure 17:
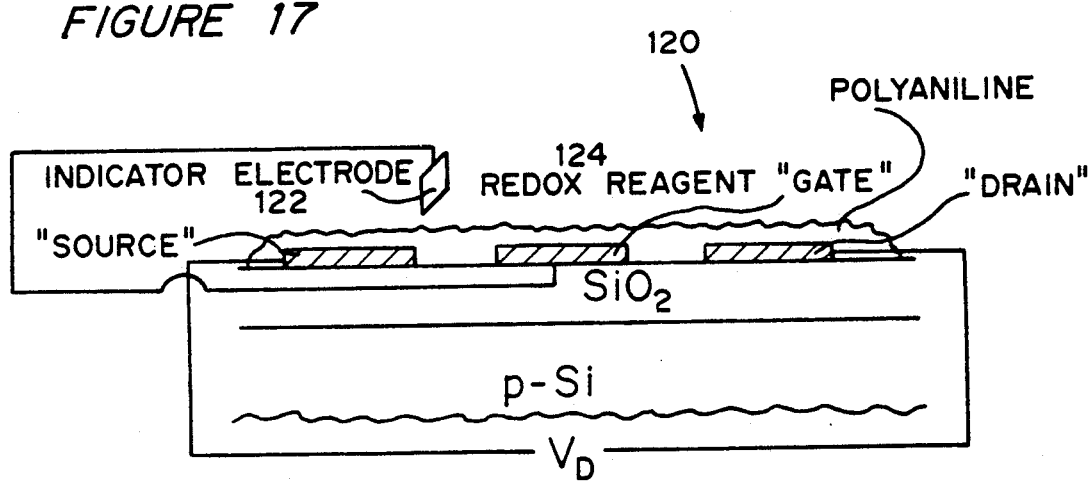
FIG. 17 is a cross-sectional view of a polyaniline-connected microelectrode array connected externally to a macroscopic indicator electrode.

As depicted in FIG. 17, the change in resistance of the polyaniline with a change in electrochemical potential can be brought about by externally connecting the polyaniline-connected microelectrode array 120 to a macroscopic indicator electrode 122 that will respond to reagents 124 other than outer-sphere reagents. When the indicator electrode 122 is platinum, the microelectrode array 120 can be equilibrated with $H^+/H_2$ since platinum equilibrates with $H^+/H_2$.

Figure 18:
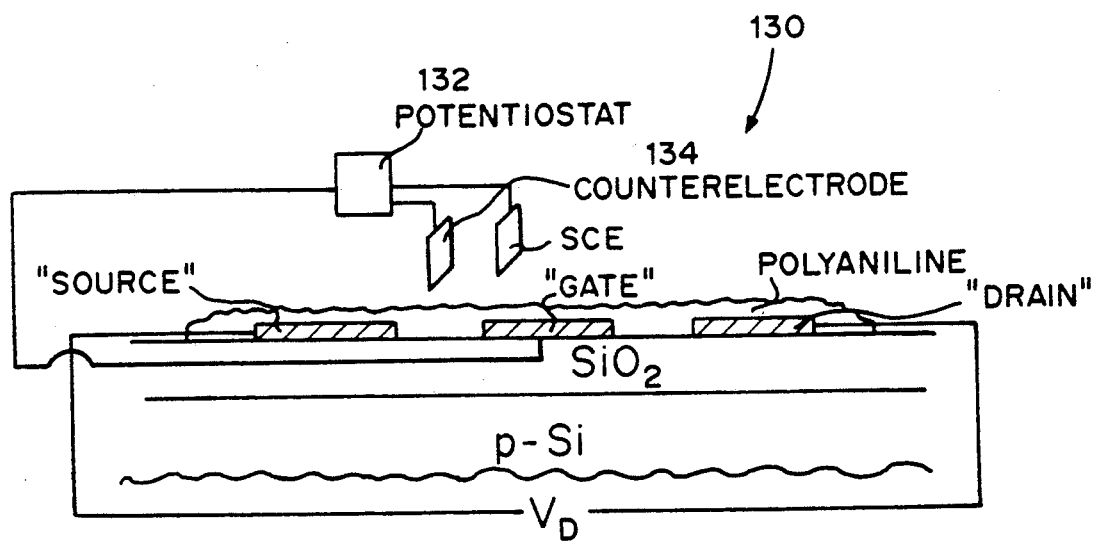
FIG. 18 is a cross-sectional view of a polyaniline-connected microelectrode array consisting of three gold microelectrodes connected to a counter-electrode, reference electrode, and potentiostat.

The device 130 in FIG. 18 is useful in characterizing the device of FIG. 17 since the potentiostat 132 and counter-electrode 134 can be used to quantitatively establish the amount of charge that is necessary to turn on the device 130. This device differs from the device 110 shown in FIG. 12A by the presence of an additional polymer-coated microelectrode and because the source and drain float.

It is also possible to chemically functionalize the polymer directly, as by the deposition of a metal such as palladium or a metal oxide onto the polyaniline connecting the microelectrodes. Palladium provides a mechanism for equilibrating the polymer with $H_2O/H_2$ and $O_2/H_2O$.

The present invention may be embodied in other specific forms without departing from the spirit and scope thereof. These and other modifications of the invention will occur to those skilled in the art. Such other embodiments and modifications are intended to fall within the scope of the appended claims.

What is claimed is:

1. A microelectronic device comprising at least two closely spaced electrically conductive electrodes on an insulating substrate overlaid with an electroactive polymer, wherein said polymer is insulating at a first redox potential conducting at a second more positive redox potential, and insulating at a third, more positive redox potential, and an electrolyte, wherein the conductivity of the electroactive polymer is altered through the electrolyte using electrochemical processes.

2. The device of claim 1 wherein said polymer is polyaniline.

3. The device of claim 1 wherein said polymer is responsive to one electron outer-sphere redox reagents.

* * * * *